United States Patent [19]

Lubisch et al.

[11] Patent Number: 5,773,439

[45] Date of Patent: Jun. 30, 1998

[54] AMIDO-QUINOXALINEDIONES, THE PREPARATION AND USE THEREOF

[75] Inventors: Wilfried Lubisch, Mannheim; Berthold Behl; Hans Peter Hofmann, both of Limburgerhof, all of Germany

[73] Assignee: BASF Aktiengesellschaft, Ludwigshafen, Germany

[21] Appl. No.: 765,260

[22] PCT Filed: Jun. 16, 1995

[86] PCT No.: PCT/EP95/02324

§ 371 Date: Dec. 20, 1996

§ 102(e) Date: Dec. 20, 1996

[87] PCT Pub. No.: WO95/35289

PCT Pub. Date: Dec. 28, 1995

[30] Foreign Application Priority Data

Jun. 22, 1994 [DE] Germany ........................ 44 22 037.7
Aug. 9, 1994 [DE] Germany ........................ 44 28 152.8

[51] Int. Cl.⁶ ...................... A61K 31/495; C07D 403/12
[52] U.S. Cl. ................... 514/249; 514/250; 544/344; 544/354
[58] Field of Search .................. 544/344, 354; 514/249, 250

[56] References Cited

U.S. PATENT DOCUMENTS 5,514,680  5/1996  Weber et al. ........................ 514/249

FOREIGN PATENT DOCUMENTS

| | | |
|---|---|---|
| 660799 | 7/1995 | Australia . |
| 2099270 | 10/1992 | Canada . |
| 260 467 | 3/1988 | European Pat. Off. . |
| 315 259 | 5/1989 | European Pat. Off. . |
| 315 959 | 5/1989 | European Pat. Off. . |
| 374 534 | 6/1990 | European Pat. Off. . |
| 377 112 | 7/1990 | European Pat. Off. . |
| 572 852 | 12/1993 | European Pat. Off. . |
| 41 35 871 | 10/1991 | Germany . |
| 43 40 045 | 11/1993 | Germany . |
| 91/13878 | 9/1991 | WIPO . |
| 92/07847 | 5/1992 | WIPO . |
| 94/00124 | 1/1994 | WIPO . |

OTHER PUBLICATIONS

*Arzneim.–Forsch./Drug Res.*, 40 (I), No. 5, 1990, pp. 511–514, Dingledine et al.
*TIPS*, 1990, vol. 11, pp. 334–338.
*Drugs of the Future*, vol. 14, No. 10, Oct. 1989, p. 1059.
*Bioorganic & Medicinal Chem. Letters*, vol. 3, No. 12, pp. 2801–2804, 1993, Epporson et al.

*Primary Examiner*—Matthew V. Grumbling
*Attorney, Agent, or Firm*—Keil & Weinkauf

[57] ABSTRACT

Novel amido-quinoxalinediones of the formula

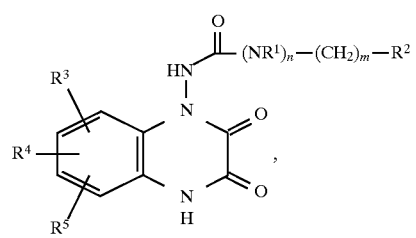

where $R^1$–$R^5$, n and m have the meanings stated in the description, and the preparation thereof are described. The compounds are suitable for controlling diseases.

3 Claims, No Drawings

AMIDO-QUINOXALINEDIONES, THE PREPARATION AND USE THEREOF

This is a national stage application filed under 35 U.S.C. §371, filed Jun. 16, 1995.

The present invention relates to novel amido-quinoxalinediones, processes for the preparation thereof and the use thereof for controlling diseases.

What are called excitatory amino acids, eg. glutamic acid, are widespread in the central nervous system. These excitatory amino acids function as transmitter substances for glutamate receptors, of which various subtypes are known. One subtype is, for example, named after the specific agonist the N-methyl-D-aspartate (NMDA) receptor. This NMDA receptor has various binding sites for agonists and antagonists. The amino acid glycine likewise binds to the NMDA receptor and modulates the effect of the natural agonist glutamic acid. Antagonists at this glycine binding site can accordingly show antagonistic effects on the NMDA receptor and inhibit "overexcitation" of this receptor.

Two other subtypes of glutamate receptors are the AMPA receptor and the kainate receptor, which are called after the respective specific agonists 2-amino-3-hydroxy-5-methyl-4-isoxazolepropionic acid (AMPA) and kainic acid. Antagonists of these receptors could, in a similar way to the NMDA receptor already mentioned, likewise inhibit "overexcitation".

Elevated glutamate levels occur in a number of neurodegenerative disorders or psychological disturbances and may lead to states of overexcitation or toxic effects in the CNS.

Antagonists of the glutamate receptor subtypes can thus be used for the treatment of these disorders. Glutamate antagonists, which include in particular NMDA antagonists and their modulators (such as glycine antagonists) and the AMPA antagonists, are therefore suitable for use for the therapy of neurodegenerative disorders (Huntington's chorea and Parkinson's disease), neurotoxic disturbances following hypoxia, anoxia or ischemia, as occur after stroke, or else as antiepileptics, antidepressants and anxiolytics (cf. Arzneim. Forschung 40 (1990) 511–514; TIPS 11 (1990) 334–338 and Drugs of the Future 14 (1989) 1059–1071).

Derivatives of quinoxaline-2,3(1H,4H)-dione II

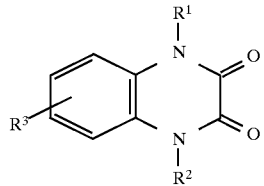

have been described in several publications, such as EP 374,534 and EP 260,467, as glutamate antagonists. Many of the known derivatives are unsubstituted in the heterocyclic quinoxaline fragment (II, $R^1$, $R^2$=hydrogen). However, some derivatives in which $R^1$ in II is a radical which is not hydrogen are also known. Thus, EP 377,112 and EP 374,534 have claimed N-hydroxyquinoxalines (II; $R^1$=$OR^4$). EP 315,959, DE 4,135,871, WO 91/13,878, WO 92/07,847 and WO 94/00,124 describe alkyl radicals as $R^1$ in II, and the alkyl chain can also be substituted by acids, esters or amides. Alkyl acids (=$R^1$) are likewise mentioned in J. R. Epperson et al. Bioorg. & Med. Chemistry Lett. 3 (1993) 2801–4. Said publications are, however, distinguished by predominantly describing alkyl esters and alkyl acids. By contrast, EP 315,259 mentions an acetamide (cf. $R^1$) (Example 24), J. R. Epperson et al. (loc. cit.) mentions an acetanilide (Example 16) and EP 572,852 mentions various amides (cf. Example 56).

Few derivatives derived from N-aminoquinoxalinedione have been disclosed in the literature to date. 1-Aminoquinoxalinedione was described by Shin, Sung-Chul et al., Taehan Hwahakhoe Chi 27 (1983) 382–4 [CA 100, 103276] and Rossi et al., Tetrahedron 24 (1968) 6395. Rossi et al. likewise prepared N-iminoquinoxalinediones. WO 93/08,173 claimed N-alkylaminoquinoxalines as glutamate antagonists, and EP 358,148 claimed N-amidoquinoxalinediones substituted by phthalimido radicals as pigments. Except in the last application mentioned, N-amidoquinoxalinediones have never been described to date. Pyrrolylquinoxalines have to date been mentioned only in EP 572,852.

We have now found novel N-amidoquinoxalinediones with novel types of actions.

The invention relates to novel amidoquinoxalinediones of the formula I

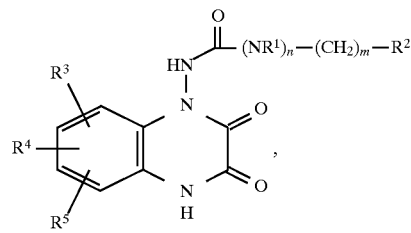

where
$R^1$ is hydrogen or $C_1$–$C_4$-alkyl,
n is 0 or 1,
m is 0, 1, 2, 3 or 4,
$R^2$ is hydrogen, branched or straight-chain $C_1$–$C_6$-alkyl or phenyl, which can be substituted by a maximum of two of the following radicals: straight-chain or branched $C_1$–$C_4$-alkyl, $OR^6$, $NH_2$, $NO_2$, $NHCOR^6$, CN, $CF_3$, $OCF_3$, —$CO_2R^6$, F, Cl, Br, I, —CO—$R^6$ or $SO_2R^6$ where $R^6$ is hydrogen, $C_1$–$C_4$-alkyl, phenyl or benzyl,
$R^3$ is fluorine, chlorine, bromine, iodine, $C_1$–$C_4$-alkyl, $OR^7$, —CO—$R^7$, $NH_2$, $NO_2$, —NH—CO—$R^7$, $CF_3$, CN or

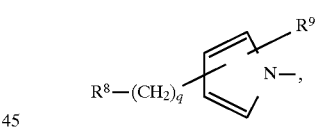

where $R^7$ is hydrogen, $C_1$–$C_4$-alkyl or $CF_3$, and q is 0, 1 or 2, and $R^8$ is H, $C_1$–$C_4$-alkyl, phenyl, phenylsulfonyl, $NO_2$, CN, —COO($CH_2$)$_r R^{10}$, —CONH($CH_2$)$_r R^{10}$, —CO—$R^{10}$, —CH=CHCONHR$^{10}$, —$CH_2$—$NR^{10}R^{11}$, —$CH_2$NH—CY—($CH_2$)$_r R^{11}$, —CH=CH—COOR$^{10}$, —CH=NOR$^{10}$, —CH=NR$^{10}$, —$CH_2$—NH—CY—Z—($CH_2$)$_r R^{11}$, —$CH_2$—NH—CO—$CF_3$,

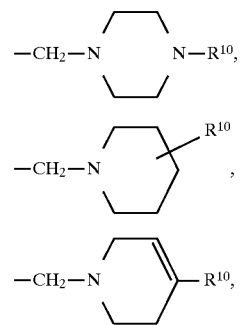

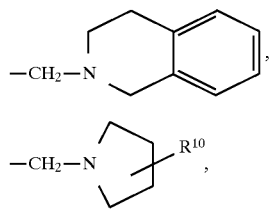

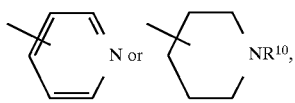

where Y is O or NH,
Z is O or NH and $R^{10}$ is hydrogen, straight-chain or branched $C_1$–$C_4$-alkyl, phenyl, benzyl, pyridyl or benzhydryl, r is 0, 1, 2, 3 or 4 and $R^{11}$ is hydrogen, straight-chain or branched $C_1$–$C_4$-alkyl, phenyl,

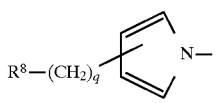

and $R^9$ is hydrogen or $C_1$–$C_4$-alkyl, and the benzene rings present in $R^8$, $R^{10}$ and $R^{11}$ can also be substituted by one or two of the following radicals: $NH_2$, $OCH_3$, $OCH_2CH_3$, Cl, Br, $OCF_3$, F, $CH_3$, $C_2H_5$, $NO_2$, —$COOR^1$, —$CONHR^1$, —$CH_2NHR^1$, —$CH_2NH$—CO—$CF_3$, —$CH_2NH$—CO—$CH_3$, —NH—$SO_2$—$CH_3$, —NH—CO—$CH_3$ or —NH—CO—$CF_3$ and $R^4$ and $R^5$, which can be identical or different, are hydrogen, $C_1$–$C_4$-alkyl, $C_1$–$C_4$-alkoxy, trifluoromethyl, trifluoromethoxy, fluorine, bromine, iodine, nitro, cyano or a fused-on benzene ring which in turn can carry up to two of the above radicals mentioned for $R^4$ and $R^5$, and the tautomeric, isomeric and enantiomeric forms thereof and the physiologically tolerated salts thereof.

Preferred amidoquinoxalinediones of the formula I are those where $R^1$ is hydrogen or $C_1$–$C_4$-alkyl,
n is 0,
m is 0, 1, 2, 3 or 4,
$R^2$ is branched or straight-chain $C_1$–$C_6$-alkyl or phenyl which can be substituted by a maximum of two of the following radicals: straight-chain or branched $C_1$–$C_4$-alkyl, $OR^6$, $NH_2$, $NO_2$, $NHCOR^6$, CN, $CF_3$, $OCF_3$, —$CO_2R^6$, F, Cl, Br, I, —CO—$R^6$ or $SO_2R^6$, where $R^6$ is hydrogen, $C_1$–$C_4$-alkyl, phenyl or benzyl,
$R^3$

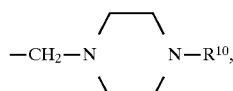

where q is 0, 1 or 2, and $R^8$ is H, $C_1$–$C_4$-alkyl, phenyl, phenylsulfonyl, $NO_2$, CN, —COO($CH_2$)$_r R^{10}$, —CONH($CH_2$)$_r R^{10}$, —CO—$R^{10}$, —CH=CHCONHR$^{10}$, —$CH_2$—NR$^{10}R^{11}$, —$CH_2$NH—CY—($CH_2$)$_r R^{11}$, —CH=CH—COOR$^{10}$, —CH=NOR$^{10}$, —CH=NR$^{10}$ —$CH_2$—NH—CY—Z—($CH_2$)$_r R^{11}$, —$CH_2$—NH—CO—$CF_3$,

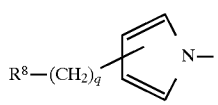

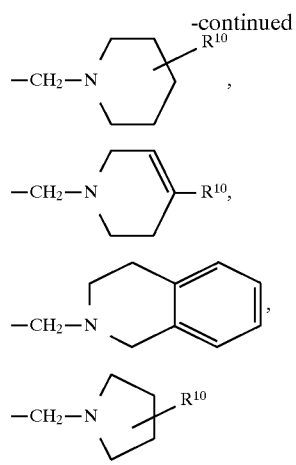

where Y is O or NH,
Z is O or NH and $R^{10}$ is hydrogen, straight-chain or branched $C_1$–$C_4$-alkyl, phenyl, benzyl, pyridyl or benzhydryl, r is 0, 1, 2, 3 or 4, and $R^{11}$ is hydrogen, straight-chain or branched $C_1$–$C_4$-alkyl, phenyl,

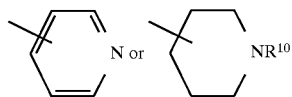

and the benzene rings present in $R^8$, $R^{10}$ and $R^{11}$ can also be substituted by one or two of the following radicals: $NH_2$, $OCH_3$, $OCH_2CH_3$, Cl, Br, $OCF_3$, F, $CH_3$, $C_2H_5$, $NO_2$, —$COOR^1$, —$CONHR^1$, —$CH_2NHR^1$, —$CH_2NH$—CO—$CF_3$, —$CH_2NH$—CO—$CH_3$, —NH—$SO_2$—$CH_3$, —NH—CO—$CH_3$ or —NH—CO—$CF_3$ and $R^4$ and $R^5$, which can be identical or different, are hydrogen, trifluoromethyl, nitro, cyano or a fused-on benzene ring.

Particularly preferred aminoquinoxalinediones of the formula I are those where $R^1$ is hydrogen or $C_1$–$C_4$-alkyl,
n is 0,
m is 0,
$R^2$ is methyl or phenyl which can be substituted by one or two straight-chain $C_1$–$C_4$-alkyl radicals,
$R^3$ is

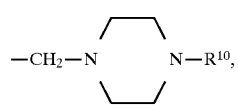

where
q is 0 and $R^8$ is H, —COO($CH_2$)$_r R^{10}$, —CONH($CH_2$)$_r R^{10}$, —$CH_2$—NR$^{10}R^{11}$, —$CH_2$NH—CY—($CH_2$)$_r R^{11}$, —CH=NOR$^{10}$, —$CH_2$—NH—CY—Z—($CH_2$)$_r R^{11}$, —$CH_2$—NH—CO—$CF_3$ or

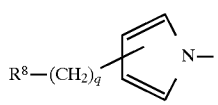

where Y is O
Z is NH and $R^{10}$ is hydrogen, straight-chain or branched $C_1$–$C_4$-alkyl, phenyl, benzyl, pyridyl or benzhydryl, r is 0, 1, 2, 3 or 4 and $R^{11}$ is hydrogen, straight-chain or branched $C_1$–$C_4$-alkyl, phenyl or

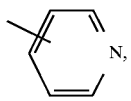

and the benzene rings present in $R^8$, $R^{10}$ and $R^{11}$ can also be substituted by one or two of the following radicals: $NH_2$, $OCH_3$, $OCH_2CH_3$, Cl, Br, $OCF_3$, F, $CH_3$, $C_2H_5$, $NO_2$, —$COOR^1$ or —$CONHR^1$ and $R^4$ and $R^5$, which can be identical or different, are hydrogen, trifluoromethyl or a fused-on benzene ring.

The present N-amidoquinoxalinediones surprisingly show advantages by comparison with the abovementioned quinoxalinediones previously disclosed, in particular better activity. Thus, for example, the substance of Example 29 according to the invention (1-amido-7-pyrrolylquinoxalinedione) is distinctly more active than one of the most closely related derivatives, namely 1-carbamoyl-7-pyrrolylquinoxalinedione (cf. Example 56 in EP 572,852). This is supported by the finding of J. R. Epperson et al. (Bioorg. & Med. Chemistry Lett. 3 (1993) 2801–4) that a 1-carbamoylmethylquinoxalinedione (Compound 16) is inactive.

The 1-amidoquinoxalinediones according to the invention can be prepared in various ways.

Substituted aromatic compounds III where L is a leaving group such as halogen, $OCH_3$ or $OSO_2CF_3$ are reacted with hydrazines IV in a nucleophilic substitution to give corresponding aromatic hydrazines V (Scheme 1). Group Z in IV is an amino protective group such as trifluoroacetyl, acetyl, Boc and benzoyl. The reaction to give V takes place in solvents, preferably polar solvents such as alcohols, acetonitrile, dimethylformamide and higher polyol derivatives, at 25°–150° C., preferably at 80°–150° C., in the presence of a base such as tertiary amines and potassium carbonate.

Scheme 1

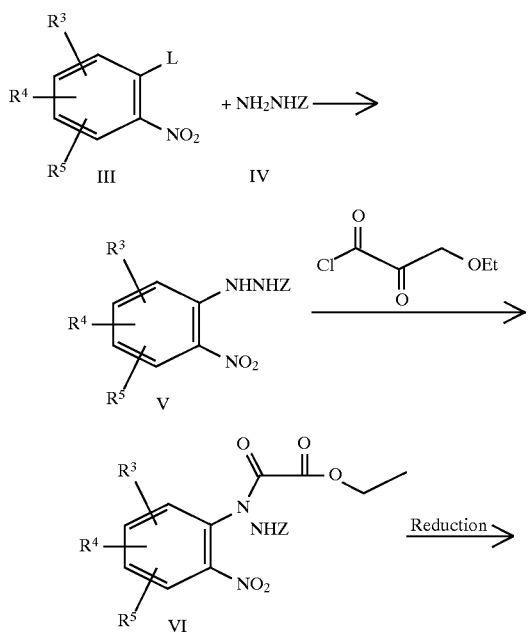

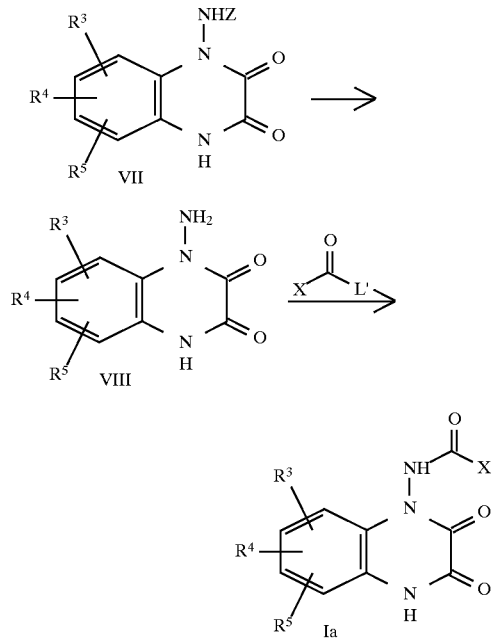

The derivative V affords with activated oxalic monoesters, such as ethyl oxalyl chloride, the anilide derivatives VI. This amide formation is carried out by conventional processes in solvents such as tetrahydrofuran, methylene chloride, dimethylformamide or pyridine with the addition, where appropriate, of bases such as triethylamine, pyridine, potassium carbonate or aqueous sodium hydroxide solution, at 0°–30° C. The nitro anilide VI is reduced to the quinoxalinedione VII either catalytically or chemically. Catalytic reduction takes place in polar solvents such as dimethylformamide, alcohols or tetrahydrofuran in the presence of catalytic amounts of palladium/carbon, platinum/carbon or similar catalysts at 25°–100° C. Reducing agents which can be used are hydrogen or hydrogen donors such as ammonium formate or hydrazine. Chemical reduction is carried out with metals such as iron and zinc or metal compounds such as tin(II) chloride in polar solvents such as water or glacial acetic acid, with or without the addition of acids such as hydrochloric acid or acetic acid, at 25°–150° C., preferably 60°–120° C.

Elimination of the protective group Z in VII to give the 1-aminoquinoxaline VIII takes place by conventional processes which depend on the protective group and are listed in Th. Green et al., "Protective Groups in Organic Synthesis", Wiley & Sons 1991, Chapter 7.

This amino derivative VIII can be reacted with activated carboxylic acid derivatives X—CO—L' (X=—$(NR^1)_n$—$(CH_2)_m$—$R^2$) to give the amido derivatives Ia according to the invention, where L' is a leaving group which can be, for example, chloride, imidazole, X—CO—O— or another group with which the acid X—CO—OH can be activated for the reaction and which are listed, inter alia, in R. C. Larock, "Comprehensive Organic Transformations", New York 1989, pages 972 et seq. These couplings are carried out by conventional processes which are detailed, for example, in Houben-Weyl, "Methoden der organischen Chemie", Volume E5, Chapter V.

The synthesis of 1-amidoquinoxalines I can also take place similar to Scheme 1 using derivatives III, as shown in Scheme 1, in which an $R^3$ radical is also linked to the aromatic system. The quinoxaline VII (see Scheme 2) is nitrated similar to conventional processes which are listed, for example, in Houben-Weyl, "Methoden zur organischen Chemie" Volume 10/1, to give IX. Nitrating agents such as potassium nitrate or nitric acid are used for this at 0°–100° C., preferably in the presence of sulfuric acid or acetic acid.

Elimination of the protective group Z to give X and introduction of the group X—CO— to give the compounds Ib according to the invention take place similar to the processes in Scheme 1 (see above).

The nitroaromatic compound IX can be reduced to the aniline X in a similar way to the reduction processes from

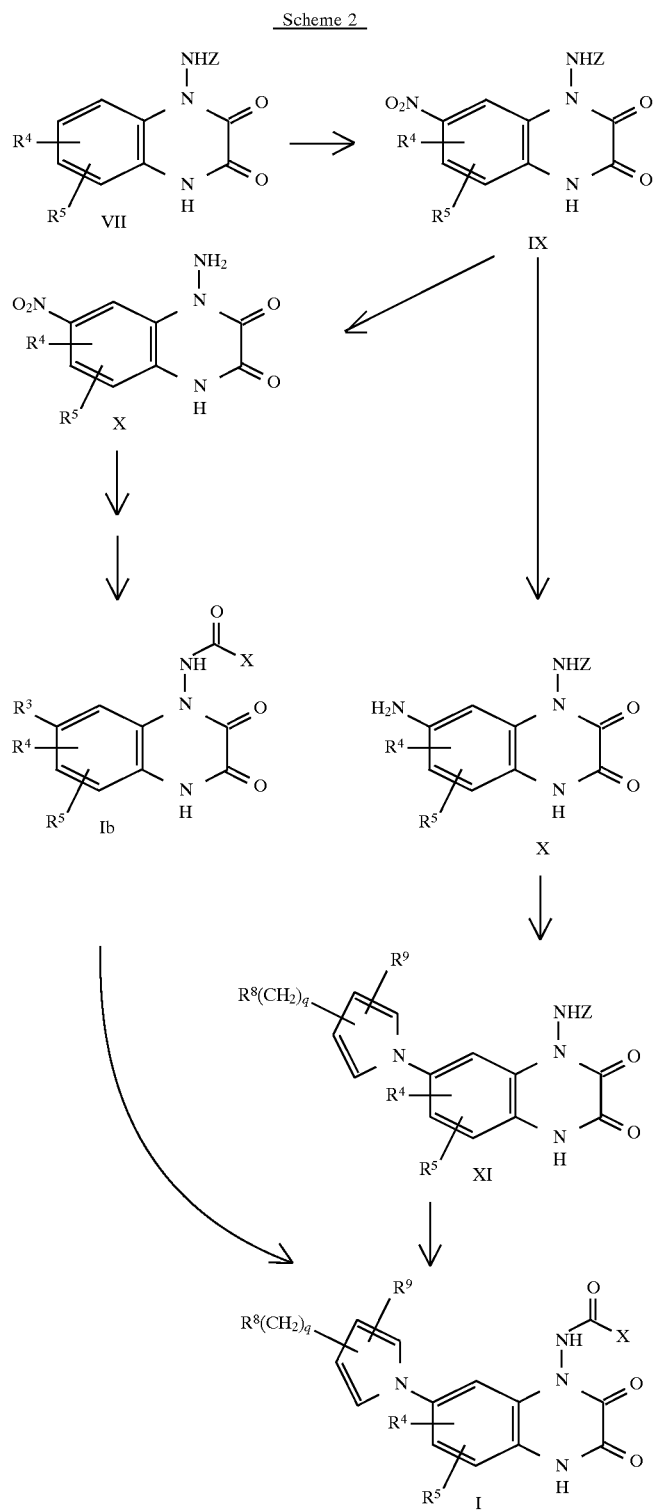

Scheme 2

Scheme 1 (step VI→VII). The aniline X is reacted with a 1,4-dicarbonyl compound such as

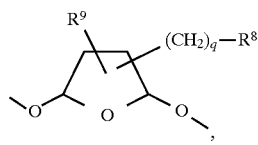

succinaldehyde derivatives or other cyclic and acyclic acetals derived therefrom to give pyrroles XI. Conventional processes are used for this, as are detailed, for example, in C. Ferri, "Reaktionen der organischen Synthese", Thieme-Verlag, 1978, pages 708 et seq., but preferably in glacial acetic acid at 60°–140° C. or in toluene/dimethylformamide mixtures with azeotropic removal of water. Removal of the protective group Z and introduction of the group X—CO— in XI to give the quinoxalinediones I according to the invention takes place in a similar way to Scheme 1 (VIII→Ib).

In the products I prepared in this way it is possible to change the substitution of the pyrrolyl ring claimed in $R^7$ in a suitable manner (Scheme 3). Thus, for example, the aldehyde can be converted by reductive amination with amines into the compounds I according to the invention. The reductive amination is generally carried out at from 5° to 80° C., preferably 10° to 30° C., in the presence of reducing agents such as sodium cyanoborohydride or hydrogen in the presence of hydrogenation catalysts such as Pd/carbon, Pt/carbon or Raney nickel, expediently in polar organic solvents such as alcohols or dimethylformamide.

The aldehyde Ic can be oxidized by conventional processes which are described, for example, in R. C. Larock, "Comprehensive Organic Transformations", 1989, VCH Publisher, pages 838 et seq., to the carboxylic acid Id according to the invention, and the oxidation is preferably carried out with potassium permanganate in solvents such as acetone at 25°–60° C. These carboxylic acids I are converted by reaction with amines $HNR^1R^2$ into the amides Ie. This coupling takes place by conventional processes which are listed, for example, in Houben-Weyl, "Methoden der organischen Chemie", Volume E5, Chapter V.

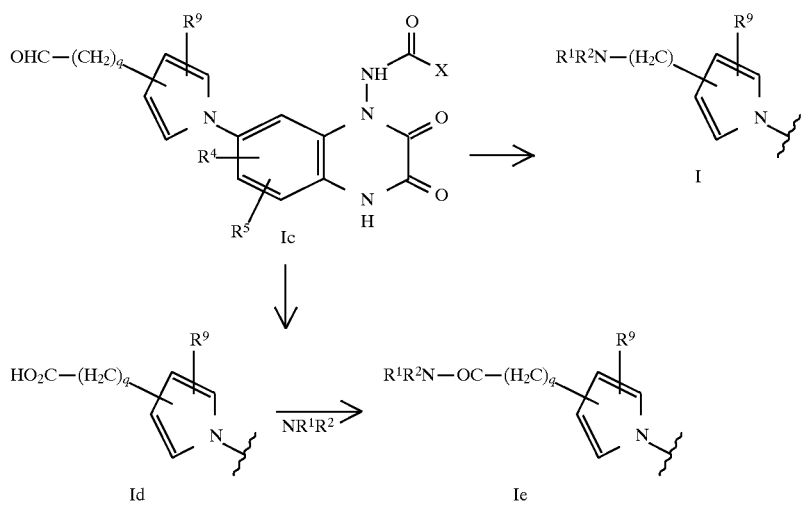

Scheme 3

Scheme 4

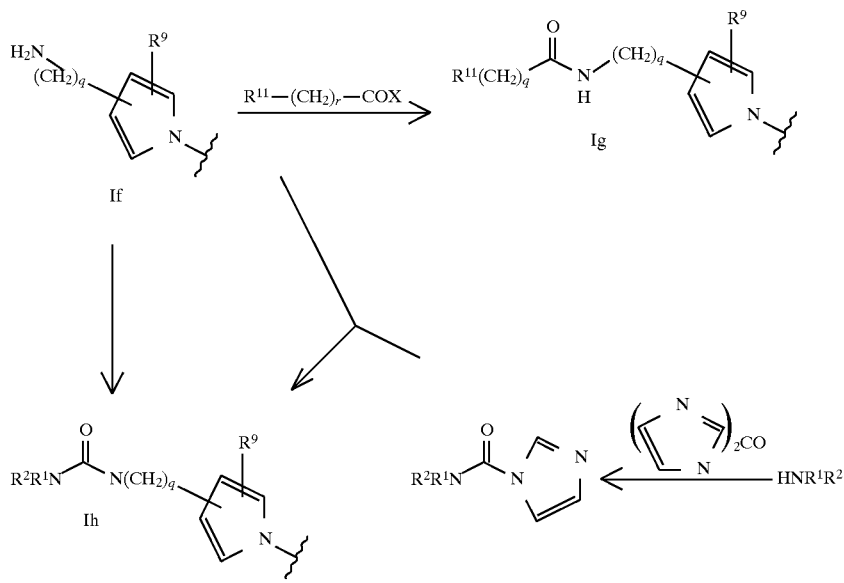

On the other hand, pyrrolylalkylamines If (see Scheme 4) obtainable in this way can be converted with acids $R^{11}(CH_2)$ $CO_2H$ which are activated in a suitable manner to $R^{11}(CH_2)$ COL" where L" is a leaving group such as azide, imidazole and others which are listed in R. C. Larock, Comprehensive Organic Transformations, New York 1989, pages 972 et seq., into the amides I" according to the invention. This coupling takes place by conventional processes as listed in, for example, Houben-Weyl "Methoden der organischen Chemie", Volume E5, Chapter V.

The pyrrolylalkylamines can likewise be reacted with isocyanates to give the ureas Ih, it also being possible to use in place of the isocyanates amines $HNHR^{10}$ which are previously reacted in a conventional way with phosgene or similar compounds such as carbonyldiimidazole. These and comparable processes are described, for example, in Houben-Weyl "Methoden der organischen Chemie", Volume E4, pages 334 et seq. These processes are carried out with or without solvent, which would preferably be dimethylformamide, at 25°–150° C.

The compounds according to the invention are antagonists of the excitatory amino acid glutamate, in particular antagonists of the glycine binding site of the NMDA receptor, of the AMPA receptor and of the kainate receptor.

The pharmacological activity of the compounds I was investigated in isolated membrane material from rat cerebra. For this purpose, the membrane material was treated in the presence of the compounds according to the invention with the radiolabeled substances $^3$H-2-amino-3-hydroxy-5-methyl-4-isoxazolepropionic acid ($^3$H-AMPA) [$^3$H]-glycine or [$^3$H]-kainate, these binding to specific receptors (AMPA, NMDA or kainate receptors). Subsequently, the radioactivity of the treated membranes was measured by scintillation counting. It was possible to determine from the bound radioactivity the amounts of bound $^3$H-AMPA, [$^3$H]-glycine or [$^3$H]-kainate, or in each case the amounts of these radiolabeled substances displaced. The dissociation constant $K_I$ (I=inhibitor) derived from this is a measure of the displacing action of the agent according to the invention and was found by iterative non-linear regression analysis using the statistical analysis system (SAS) on an IBM computer, similar to the "Ligand" program of P. J. Munson and D. Rodbard (Analytical Biochem. 107, 220 (1980), Ligand: Versatile Computerized Approach for Characterization of Ligand Binding Systems).

The following in vitro investigations were carried out:

1. Binding of $^3$H-2-amino-3-hydroxy-5-methyl-4-isoxazolepropionic acid ($^3$H-AMPA)

To prepare the membrane material, freshly removed rat cerebra were homogenized together with 15 times the volume of a buffer solution A comprising 30 mM α,α,α-tris (hydroxymethyl)methylamine hydrochloride (TRIS-HCl) and 0.5 mM ethylenediaminetetraacetic acid (EDTA), pH 7.4, using an Ultra-Turrax®. The suspension was centrifuged at 48,000 g for 20 min. After removal of the supernatant liquid, the protein-containing membrane material contained in the sediment was washed three times by suspension in buffer solution A and subsequent centrifugation at 48,000 g for 20 minutes each time. The membrane material was then suspended in 15 times the volume of buffer solution A and incubated at 37° C. for 30 min. The protein material was subsequently washed twice by centrifugation and suspension and stored at –70° C. until used.

For the binding assay, the protein material was thawed at 37° C. and washed twice by centrifugation at 48,000 g (20 min) and subsequent suspension in a buffer solution B comprising 50 mM TRIS-HCl, 0.1M potassium thiocyanate and 2.5 mM calcium chloride, pH 7.1. Subsequently, 0.25 mg of membrane material, 0.1 μCi of $^3$H-AMPA (60 Ci/mmol) and compound I were dissolved in 1 ml of buffer solution B and incubated on ice for 60 min. The incubated solution was filtered through a CF/B filter (from Whatman) which had previously been treated with a 0.5% strength aqueous solution of polyethyleneimine for at least 2 hours. The membrane residue was subsequently washed with 5 ml of cold buffer solution B in order to separate bound and free $^3$H-AMPA from one another. After measurement of the radioactivity of the bound $^3$H-AMPA in the membrane material by scintillation counting, the $K_I$ was determined by regression analysis of the displacement plots.

A $K_I$ of <10 μM was found for 1-benzamido-7-(1-pyrrolyl)-6-trifluoromethylquinoxaline-2,3-(1H,4H)-dione (Example 29) and 1-benzamido-6-trifluoromethylquinoxaline-2,3(1H,4H)-dione (Example 1), and thus both are more active than the substance of Example 56 in EP 572,852 and compound 16 which is mentioned on page 4 in line 24.

2. Binding of [$^3$H]-glycine

To prepare membranes for the $^3$H-glycine binding assay, freshly removed rat hippocampi were homogenized in 10 times the volume of preparation buffer (50 mM Tris-HCl, 10 mM EDTA) using a Potter homogenizer. The homogenate was centrifuged at 48,000×g for 20 min. The supernatant was discarded, and the membranes contained in the pellet were washed 2× by resuspension and centrifugation at 48,000×g (20 minutes each time). The resuspended membranes were frozen in liquid nitrogen and thawed again at 37° C. After another washing step, the membrane suspension was incubated in a shaking waterbath at 37° C. for 15 min. After a further 4 washing steps (in each case centrifugation at 48,000×g for 20 minutes and resuspension in preparation buffer), the membranes were frozed at -70° C. until used further.

The frozen membranes were thawed at 37° C. and washed 2× by centrifugation at 48,000×g (20 min) and subsequent resuspension in binding buffer (50 mM Tris-HCl pH 7.4; 10 mM MgCl$_2$). An incubation mixture contained 0.25 mg of protein (membranes), 25 nM $^3$H-glycine (16 Ci/mmol) and the substances to be tested in a total of 0.5 ml of binding buffer. The non-specific binding was determined by adding 1 mM glycine. After incubation at 4° C. for 60 min, bound and free ligand were separated from one another by filtration through GF/B filters and subsequent washing with about 5 ml of ice-cold binding buffer. The radioactivity remaining on the filters is determined by liquid scintillation counting. The dissociation constants were calculated from the displacement plots using an iterative non-linear fitting program or in accordance with the Cheng and Prusoff equation.

3. Binding of [$^3$H]-kainate

To prepare membranes for the [$^3$H]-kainate binding assay, freshly removed rat cerebra were homogenized in preparation buffer (30 mM Tris-HCl pH 7.4, 0.5 mM EDTA) in 15 times the volume using an Ultra-Turrax®. The homogenate was centrifuged at 48,000×g for 20 min. The supernatant was discarded, and the membranes contained in the pellet were washed a total of 3× by resuspension in preparation buffer and centrifugation at 48,000×g at 20 min each time. After the third washing step, the membranes were incubated at 37° C. Subsequently, the membranes were washed 2× by centrifugation and resuspension and stored at -70° C. until used further.

The frozen membranes were thawed at 37° C., suspended in binding buffer (50 mM Tris-HCl pH 7.4) and centrifuged at 48,000×g for 20 min. The membranes present in the pellet were again resuspended in binding buffer. An incubation mixture contains 0.25 mg of protein (membranes), 0.058 μCi of [$^3$H]-kainate (58 Ci/mmol) and the substances to be tested in a total of 1 ml of binding buffer. The non-specific binding was determined in the presence of 0.1 mM glutamate. After incubation on ice for 60 min, bound and free ligand were separated from one another by filtration through CF/B filters and subsequent washing with 5 ml of ice-cold binding buffer. The CF/B filters had previously been treated with 0.5% polyethyleneimine for at least 2 h. The analysis of the displacement plots and calculation of the dissociation constants took place by a non-linear fitting program or in accordance with the Cheng and Prusoff equation.

The compounds I according to the invention are suitable as drugs for human and veterinary medicine and can be used for the production of drugs for the treatment of neurodegenerative disorders and neurotoxic disturbances of the central nervous system and for producing antiepileptics, anxiolytics and antidepressants.

The pharmaceutical compositions according to the invention contain besides the conventional pharmaceutical ancillary substances a therapeutically effective amount of the compounds I. For local external use, eg. in dusting powders and ointments, the agents can be present in the usual concentrations. As a rule, the agents are present in an amount of from 0.0001 to 1% by weight, preferably 0.001 to 0.1% by weight.

For internal use, the preparations are administered in single doses. From 0.1 to 100 mg per kg of body weight are given in a single dose. The compositions can be administered in one or more dosages each day depending on the nature and severity of the disorders.

The pharmaceutical compositions according to the invention contain besides the agent the customary excipients and diluents appropriate for the required mode of administration. For local external use it is possible to use pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Suitable examples for internal use are lactose, propylene glycol, ethanol, starch, talc and polyvinylpyrrolidone.

It is furthermore possible for antioxidants such as tocopherol and butylated hydroxyanisole and butylated hydroxytoluene, flavor-improving additives, stabilizers, emulsifiers and lubricants to be present.

The substances present in the composition besides the agent, and the substances used to produce the pharmaceutical composition, are toxicologically acceptable and compatible with the agent in each case. The pharmaceutical compositions are produced in a conventional way, eg. by mixing the agent with the usual excipients and diluents.

The pharmaceutical compositions can be administered in various ways, such as orally, parenterally, subcutaneously, intraperitoneally and topically. Thus, possible presentations are tablets, emulsions, solutions for infusion and injection, pastes, ointments, gels, creams, lotions, dusting powders and sprays.

EXAMPLES

Example 1

1-Benzamido-6-trifluoromethylquinoxaline-2,3(1H,4H)-dione

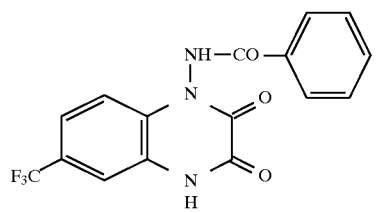

a) N'-(2-Nitro-4-trifluoromethylphenyl)-benzhydrazide:

100 g (0.44 mol) of 4-chloro-3-nitrobenzotrifluoride, 31 g (0.22 mol) of potassium carbonate and 90 g (0.66 mol) of benzhydrazide in 450 ml of dimethylformamide/water (8/1) were heated at 110° C. for 3 h. The mixture was then poured into 5 l of ice-water. The precipitate was filtered off with suction, washed with a large amount of water and dried to afford 133 g (93%) of product, melting point 200°–201° C.

$^1$H-NMR (D$_6$DMSO): δ=7.3 (1H); 7.5–7.7 (3H); 7.9 (1H); 8.0 (2H); 8.4 (1H); 9.9 (1H) and 11.0 (1H) ppm b) 1-Benzamido-6-trifluoromethylquinoxaline-(2,3)1H,4H-dione:

130 g (0.43 mol) of the product obtained in a) and 110 ml (0.8 mol) of triethylamine, dissolved in 1300 ml of anhydrous tetrahydrofuran, were added dropwise at 0° C. to 47 ml (0.44 mol) of ethyl oxalyl chloride dissolved in 200 ml of tetrahydrofuran. After 30 min, the mixture was filtered and the filtrate was concentrated under reduced pressure.

The residue (about 190 g) was taken up in 2000 ml of glacial acetic acid and heated to reflux. Then 90 g (1.6 mol) of iron powder were cautiously added in portions. The mixture was then filtered hot. The product crystallized out of the cooled filtrate and was filtered off with suction and washed with water. 101 g (81%) were obtained of melting point >270° C.

$^1$H-NMR (D$_6$-DMSO): δ=7.4–7.8 (6H); 8.1 (2H) and ca. 12.5 (broad) ppm

Example 2

7-Nitro-1-(3-nitrobenzamido)-6-trifluoromethylquinoxaline-2,3(1H,4H)-dione

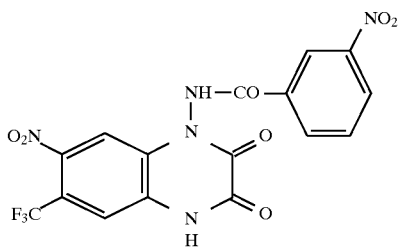

180 g (0.52 mol) of the substance of Example 1 were dissolved in 1000 ml of concentrated sulfuric acid and, at 0° C., 104.2 g (1.04 mol) of potassium nitrate were added in portions. The mixture was stirred at 0° C. for 1 h. The mixture was then poured onto ice, and the resulting precipitate was filtered off with suction and recrystallized from methanol. 161 g (73%) of product of melting point 197°–199° C. were obtained.

$^1$H-NMR (D$_6$-DMSO): δ=7.7 (1H); 7.9 (1H); 8.3 (1H); 8.45 (1H); 8.5 (1H); 8.9 (1H) and 12.5 (broad) ppm Example 3

7-Nitro-1-trifluoracetamido-6-trifluoromethylquinoxaline-2,3(1H,4H)-dione

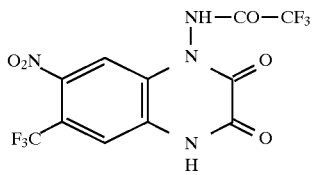

a) 1-Amino-7-nitro-6-trifluoromethylquinoxaline-2,3(1H,4H)-dione 64 g (0.15 mol) of the substance of Example 2 were added to 275 ml of 90% strength sulfuric acid and kept at 80° C. for 3 h. The reaction mixture was then poured into ice-water and the aqueous phase was extracted with ethyl acetate. The organic phase was dried and concentrated under reduced pressure. 32.3 g (77%) of product of melting point >250° C. were obtained.

$^1$H-NMR (D$_6$-DMSO): δ=6.0 (2H); 7.6 (1H); 8.35 (1H) and 12.5 (broad) ppm b) 7-Nitro-1-trifluoroacetamido-6-trifluoromethylquinoxaline-2,3(1H,4H)-dione 1.1 ml (7.6 mmol) of trifluoroacetic anhydride dissolved in 10 ml of tetrahydrofuran were added dropwise to 2.0 g (6.9 mmol) of the product obtained in a) in 50 ml of anhydrous tetrahydrofuran at 0° C. The mixture was stirred at room temperature for 16 h and then concentrated under reduced pressure. 2.3 g (89%) of product of melting point >250° C. were obtained.

$^1$H-NMR (D$_6$-DMSO): δ=7.7 (1H); 8.2 (1H) and ca. 12.7 (broad) ppm

Example 4

7-Amino-1-trifluoroacetamido-6-trifluoromethylquinoxaline-2,3(1H,4H)-dione

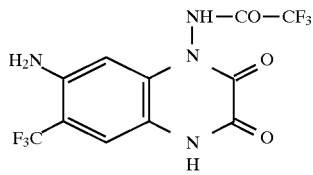

2.1 g (5.4 mmol) of the substance of Example 3 were hydrogenated in 300 ml of tetrahydrofuran/methanol (1/1) in the presence of 0.5 g of palladium/carbon (10%). The mixture was then filtered and the filtrate was concentrated under reduced pressure. 2.0 g (96%) of product of melting point >250° C. were obtained.

$^1$H-NMR (D$_6$-DMSO): δ=4.5 (2H); 6.7 (1H); 7.1 (1H), ca. 8.9 (broad, 1H) and ca. 12.7 (broad) ppm Example 5

7-(2,5-Dimethyl-1-pyrrolyl)-1-(trifluoroacetamido)-6-trifluoromethylquinoxaline-2,3(1H,4H)-dione

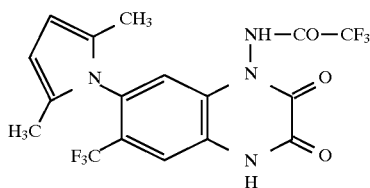

14.0 g (39.3 mmol) of the substance of Example 4 and 300 ml of glacial acetic acid were heated to 80° C. Then 4.5 g (39.3 mmol) of 2,5-hexanedione were added. After 20 min, the mixture was cooled and concentrated under reduced pressure. 13.1 g (77%) of product were obtained.

$^1$H-NMR (D$_6$-DMSO): δ=1.7 (6H); 5.8 (2H); 7.0 (1H); 7.6 (1H) and ca. 12.3 (broad) ppm Example 6

7-(1-Pyrrolyl)-1-trifluoroacetamido-6-trifluoromethylquinoxaline-2,3(1H,4H)-dione

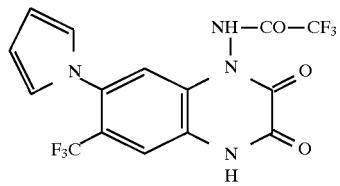

13.0 g (36.5 mmol) of the substance of Example 4 and 4.8 g (36.5 mmol) of 2,5-dimethoxytetrahydrofuran were reacted as in Example 6. 11.9 g (81%) of product of melting point >250° C. were obtained.

$^1$H-NMR (D$_6$-DMSO): δ=6.7 (2H), 6.9 (2H), 7.4 (1H); 7.6 (1H) and ca. 12.5 (broad) ppm Example 7

1-Acetamido-7-(1-pyrrolyl)-6-trifluoromethylquinoxaline-2,3-(1H,4H)-dione

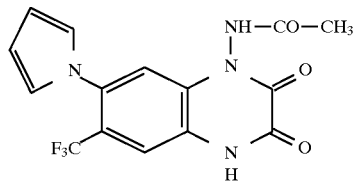

a) 1-Amino-7-(1-pyrrolyl)-6-trifluoromethylquinoxaline-2,3-(1H,4H)-dione 11 g (27.1 mmol) of Example 6 were dissolved in 150 ml of ethanol, and 17.1 g (54.2 mmol) of barium hydroxide octahydrate dissolved in 200 ml of water were added. The mixture was stirred at room temperature for 16 h and then neutralized with 2M hydrochloric acid and subsequently the aqueous phase was extracted with ethyl acetate. The organic phase was dried and concentrated under reduced pressure. 6.6 g (80%) of product were obtained.

$^1$H-NMR (D$_6$-DMSO): δ=6.6 (2H); 6.9 (2H); 7.4 (1H); 7.65 (1H) and ca. 12.5 (broad) ppm b) 1-Acetamido-7-(1-pyrrolyl)-6-trifluoromethylquinoxaline-2,3-(1H,4H)-dione 1.0 g (3.2 mmol) of the substance obtained in a) and 0.4 ml (3.6 mmol) of acetic anhydride were refluxed in 20 ml of glacial acetic acid for 3 h. The mixture was then concentrated under reduced pressure and purified by chromatography (eluent: toluene/acetone/glacial acetic acid=10/10/1). 0.83 g (74%) of product of melting point >185° C. were obtained.

$^1$H-NMR (D$_6$-DMSO): δ=2.1 (3H), 6.2 (2H); 6.8 (2H); 7.2 (1H); 7.6 (1H); 11.1 (1H) and ca. 12.5 (broad) ppm Example 8

1-Acetamido-7-(2,5-dimethyl-1-pyrrolyl)-6-trifluoromethylquinoxaline-2,3(1H,4H)-dione

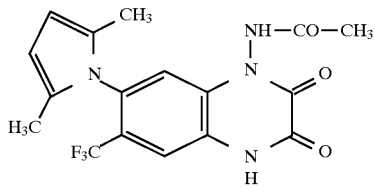

a) 1-Amino-7-(2,5-dimethyl-1-pyrrolyl)-6-trifluoromethylquinoxaline-2,3(1H,4H)-dione 12.7 g (29.2 mmol) of Example 5 were stirred in 250 ml of 0.5M hydrochloric acid at room temperature for 16 h. The mixture was then neutralized by adding dilute sodium hydroxide solution and extracted with ethyl acetate. The organic phase was dried and concentrated under reduced pressure. The residue was purified by chromatography (eluent: toluene/acetone/glacial acetic acid=10/10/1). 7.2 g (74%) of product were obtained and immediately reacted further.

b) 1-Acetamido-7-(2,5-dimethyl-1-pyrrolyl)-6-trifluoromethylquinoxaline-2,3(1H,4H)-dione 1.3 g (3.8 mmol) of the product obtained in a) and 0.4 ml (4.2 mmol) of acetic anhydride were refluxed in 50 ml of glacial acetic acid for 1 h. The mixture was then concentrated under reduced pressure and the residue was treated with ether. The product was filtered off with suction. 1.4 g (96%) were obtained. Melting point >150° C.

$^1$H-NMR (D$_6$-DMSO): δ=1.8 (3H); 1.85 (3H); 2.1 (3H); 5.8 (2H); 7.2 (1H); 8.7 (1H), 11.1 (1H) and ca. 12.5 (broad) ppm Example 9

1-Benzamido-7-nitro-6-trifluoromethylquinoxaline-2,3(1H,4H)-dione

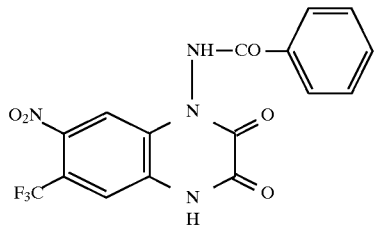

2.0 g (6.7 mmol) of the product obtained in Example 3a and 3.1 g (13.4 mmol) of benzoic anhydride were heated at 110° C. for 10 min, during which the reaction mixture crystallized completely. After cooling, the mixture was treated with ether and filtered with suction. 2.4 g (89%) of product of melting point 196°–197° C. were obtained.

$^1$H-NMR (D$_6$-DMSO): δ=7.5–7.8 (4H); 8.0 (2H); 8.1 (1H); 12 (1H) and 12,8 (broad) ppm Example 10

N-(7-Nitro-6-trifluoromethylquinoxaline-2,3(1H,4H)-dion-1-yl)-N'-phenylurea

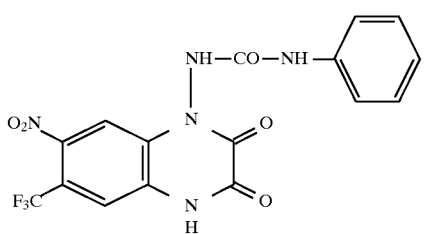

2.3 g (7.9 mmol) of the product obtained in Example 3a, 1.0 g (8.7 mmol) of phenyl isocyanate and a spatula tip of 4-(N,N-dimethylamino)pyridine were heated in 10 ml of anhydrous dimethylformamide at 130° C. for 90 min. After cooling, the mixture was partitioned between ethyl acetate and water, and the organic phase was dried and concentrated under reduced pressure. The residue was crystallized from methylene chloride/n-pentane, resulting in 1.8 g (57%) of product of melting point >240° C.

$^1$H-NMR (D$_6$-DMSO): δ=7.0 (1H); 7.3 (2H); 7.4 (2H); 7.7 (1H); 8.2 (1H); 9.3 (broad, 1H); 9.5 (1H) and ca. 12.7 (broad) ppm

Example 11

7-Amino-1-benzamido-6-trifluoromethylquinoxaline-2,3 (1H,4H)-dione

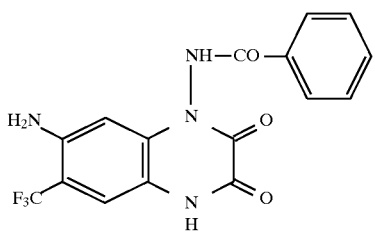

2.2 g (5.6 mmol) of the product of Example 9 were dissolved in 200 ml of methanol and, after addition of 0.5 g of palladium/carbon (10%), hydrogenated. The mixture was then filtered and the filtrate was concentrated under reduced pressure. 1.9 g (94%) of product of melting point >250° C. were obtained.

$^1$H-NMR (D$_6$-DMSO): δ=5.6 (2H); 6.7 (1H); 7.3 (1H); 7.5–7.8 (3H); 8.0 (2H); 11.7 (1H) and ca. 12.2 (broad) ppm

Example 12

N-(7-Amino-6-trifluoromethylquinoxaline-2,3(1H,4H)-dion-1-yl)-N'-phenylurea

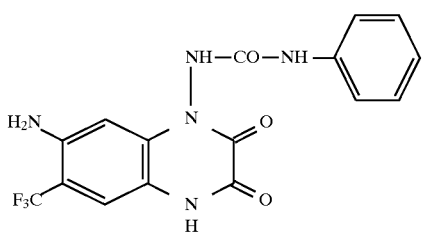

1.2 g (22 mmol) of iron powder were added in portions to 1.5 g (3.7 mmol) of the substance of Example 10 in 50 ml of glacial acetic acid at about 120° C. (reflux). The mixture was then cooled and the precipitate was filtered off with suction. The filtrate was concentrated under reduced pressure and the resulting precipitate was treated with ether. The product obtained in this way was filtered off with suction. The yield obtained was 1.3 g (94%), melting point >250° C.

$^1$H-NMR (D$_6$-DMSO): δ=5.6 (2H); 6.95 (1H); 7.0 (1H); 7.1–7.5 (5H); 8.4 (1H); 8.8 (1H) and ca. 12.2 (broad) ppm

Example 13

1-Phenylacetamido-7-nitro-6-trifluoromethylquinoxaline-2,3-(1H,4H)-dione

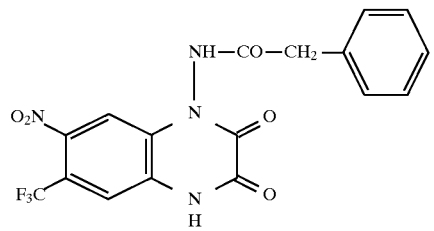

3.0 g (10.3 mmol) of the substance of Example 3a and 4.9 g (20.6 mmol) of phenylacetic anhydride were reacted as in Example 9. 3.6 g (86%) of product of melting point 232°–233° C. were obtained.

$^1$H-NMR (D$_6$-DMSO): δ=3.8 (2H); 7.1–7.5 (5H); 7.7 (1H); 7.9 (1H), 11.5 (1H) and 12,8 (1H) ppm

Example 14

7-Nitro-1-(o-toluamido)-6-trifluoromethylquinoxaline-2,3-(1H,4H)-dione

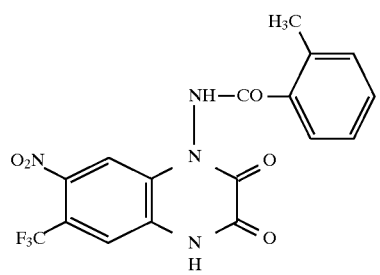

4.9 g (20.6 mmol) of o-toluic anhydride and 3.0 g (10.3 mmol) of the substance of Example 3a were reacted as in Example 9. 4.1 g (97%) of product of melting point 253°–254° C. were obtained.

$^1$H-NMR (D$_6$-DMSO): δ=2.4 (3H); 7.3–7.5 (3H); 7.6–7.8 (2H); 8.1 (1H), 11.8 (1H) and 12.9 (broad) ppm

Example 15

1-(4-Methoxybenzamido)-7-nitro-6-trifluoromethylquinoxaline-2,3-(1H,4H)-dione

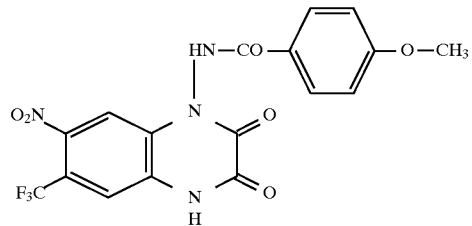

5.8 g (19.3 mmol) of 4-methoxybenzoic anhydride and 2.8 g (9.7 mmol) of the substance of Example 3a were reacted as in Example 9. 3.2 g (77%) of product of melting point >240° C. were obtained.

$^1$H-NMR (D$_6$-DMSO): δ=3.9 (3H); 7.1 (2H); 7.7 (1H); 8.05 (2H); 8.1 (1H); 11.8 (broad) and ca. 12.7 (broad) ppm Example 16

7-Nitro-6-trifluoromethyl-1-(4-trifluoromethylbenzamido)quinoxaline-2,3(1H,4H)-dione

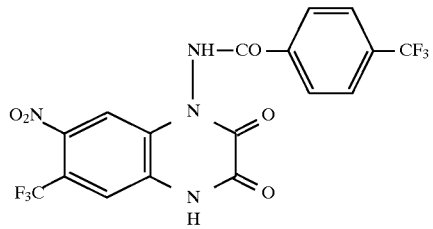

2.7 g (9.5 mmol) of the substance of Example 3a and 3.8 g (9.5 mmol) of p-trifluoromethylbenzoic anhydride were reacted as in Example 9. 3.9 g (91%) of product of melting point >230° C. were obtained.

$^1$H-NMR (D$_6$-DMSO): δ=7.7 (1H); 8.0 (2H); 8.75 (3H); 12.2 (1H) and 12.9 (1H) ppm Example 17

1-Benzamido-7-(3-formyl-1-pyrrolyl)-6-trifluoromethylquinoxaline-2,3(1H,4H)-dione

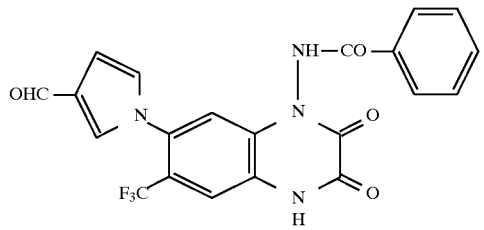

1.8 g (4.9 mmol) of Example 11 and 0.8 g (4.9 mmol) of 2,5-dimethoxytetrahydrofuran-3-carbaldehyde were refluxed in 40 ml of glacial acetic acid for 30 min. The mixture was then concentrated under reduced pressure and the residue was purified by chromatography (eluent: toluene/acetone/glacial acetic acid=40/40/1). Yield: 2.0 g (91%), melting point >210° C.

$^1$H-NMR (D$_6$-DMSO): δ=6.6 (1H); 7.1 (1H); 7.5–7.75 (5H); 7.8 (1H); 8.0 (2H); 9.75 (1H); 11.8 (broad) and 12.8 (broad) ppm Example 18

N-(7-(3-Formyl-1-pyrrolyl)-6-trifluoromethylquinoxaline-2,3-(1H,4H)-dion-1-yl)-N'-phenylurea

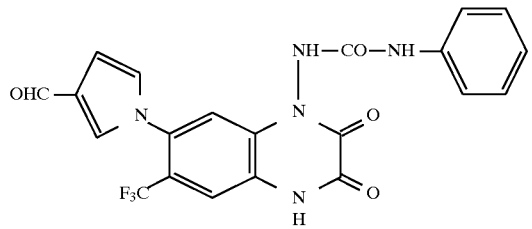

1.1 g (2.9 mmol) of the substance of Example 12 and 0.46 g 2.9 mmol) of 2,5-dimethoxytetrahydrofuran-3-carbaldehyde were reacted as in Example 17. Yield: 1.05 g (81%), melting point >250° C.

$^1$H-NMR (D$_6$-DMSO): δ=6.6 (1H); 6.9–7.1 (2H); 7.3 (2H); 7.4 (2H); 7.6 (1H); 7.7 (1H); 7.8 (1H); 9.2 (broad); 9.4 (broad); 9.8 (1H) and ca. 12,7 (broad) ppm Example 19

1-Benzamido-7-(3-(4-benzyl-1-piperazinylmethyl)-1-pyrrolyl)-6-trifluoro-methylquinoxaline-2,3(1H,4H)-dione

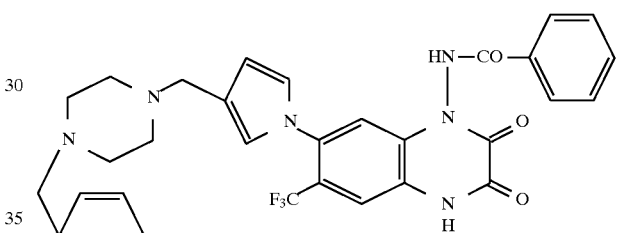

1.3 g (2.9 mmol) of the product 17, 1.0 g (5.9 mmol) of 4-benzylpiperazine and 0.35 g (5.9 mmol) of glacial acetic acid were dissolved in dimethylformamide/ethanol (1:1) and, at room temperature, 0.18 g (2.9 mmol) of sodium cyanoborohydride was added in portions. The mixture was stirred for 16 h and then concentrated under reduced pressure, and the residue was partitioned between ethyl acetate and aqueous sodium bicarbonate solution. The organic phase was dried and purified by chromatography (eluent: toluene/methanol/dimethylformamide/glacial acetic acid=10/7/1/1). Yield: 0.83 g (47%); melting point 199°–201° C.

$^1$H-NMR (D$_6$-DMSO): δ=2.3–2.6 (8H); 3.4 (4H); 6.1 (1H); 6.75 (1H); 6.8 (1H); 7.2–7.4 (6H); 7.5 (2H); 7.6 (1H); 7.65 (1H); 8.0 (2H) and ca. 12 (broad) ppm Example 20

1-Benzamido-7-(3-(N-benzylaminomethyl)-1-pyrrolyl)-6-trifluoromethylquinoxaline-2,3(1H,4H)-dione

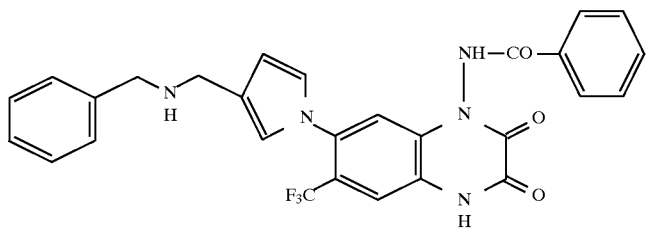

1.3 g (2.9 mmol) of the substance of Example 17 and 0.31 g (2.9 mmol) of benzylamine were reacted as in Example 19. Yield: 0.6 g (39%), melting point >235° C.

$^1$H-NMR (D$_6$-DMSO, CD$_3$COOD): δ=3.4–3.6 (4H); 6.2 (1H); 6.75 (1H); 6.8 (1H); 7.2–7.4 (6H); 7.5 (2H); 7.6 (1H); 7.7 (1H); 8,0 (2H) and ca. 12 (broad) ppm

Example 21

7-Amino-1-phenylacetamido-6-trifluoromethylquinoxaline-2,3-(1H,4H)-dione

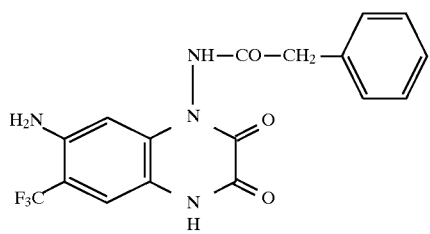

3.4 g (8.3 mmol) of the substance of Example 13 were reduced with 2.8 g (49.9 mmol) of iron powder as in Example 12. Yield: 2.3 g (75%), melting point >200° C.

$^1$H-NMR (D$_6$-DMSO): δ=3.75 (2H); 5.6 (2H); 6.7 (1H); 7.2–7.5 (6H); ca. 11.3 (1H) and ca. 12 (broad) ppm

Example 22

7-Amino-1-(2-methylbenzamido)-6-trifluoromethylquinoxaline-2,3-(1H,4H)-dione

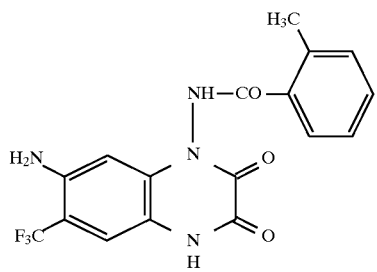

3.6 g (8.8 mmol) of the substance of Example 14 were reduced with 3 g (53 mmol) of iron powder as in Example 12. Yield: 2.9 g (88%), melting point >250° C.

$^1$H-NMR (D$_6$-DMSO): δ=2.5 (3H); 5.7 (2H); 6.9 (1H); 7.3 (1H); 7.3–7.6 (3H); 7.8 (1H); 11.5 (broad) and 12 (broad) ppm

Example 23

7-Amino-1-(4-methoxybenzamido)-6-trifluoromethylquinoxaline-2,3(1H,4H)-dione

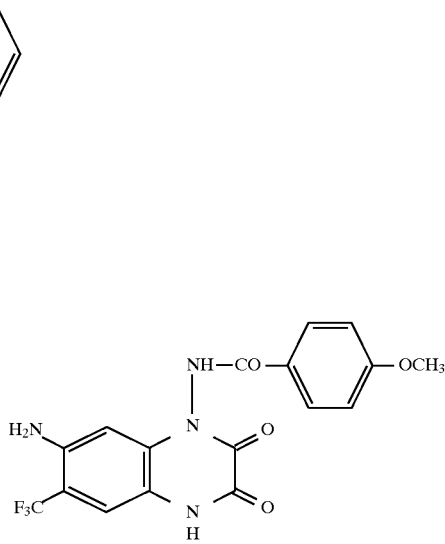

2.7 g (6.4 mmol) of the substance of Example 15 were reduced with 2.1 g (38.2 mmol) of iron powder as in Example 12. Yield: 2.3 g (92%), melting point >250° C.

$^1$H-NMR (D$_6$-DMSO): δ=3.9 (3H); 5.6 (2H); 6.8 (1H); 7.1 (2H); 7.25 (1H); 8.0 (2H); 11,5 (broad) and 12.0 (broad) ppm

Example 24

7-Amino-6-trifluoromethyl-1-(4-trifluoromethylbenzamido)quinoxaline-2,3(1H,4H)-dione

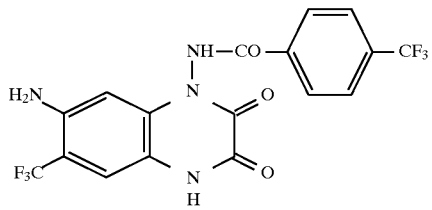

3.7 g (8.0 mmol) of the substance of Example 16 were reduced with 2.7 g (48.0 mmol) of iron powder as in Example 12.

Yield: 2.7 g (80%), melting point >250° C.

$^1$H-NMR (D$_6$-DMSO): δ=5.6 (2H); 6.8 (1H); 7.3 (1H); 8.0 (2H); 8.25 (2H); 12.0 (1H) and 12.2 (1H) ppm

Example 25

1-Phenylacetamido-7-(3-formyl-1-pyrrolyl)-6-trifluoromethylquinoxaline-2,3(1H,4H)-dione

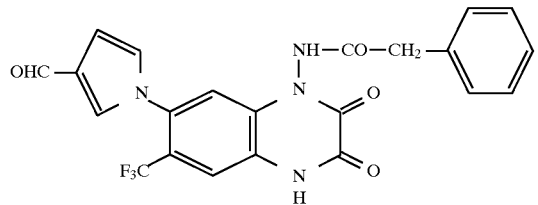

2.1 g (5.6 mmol) of the substance of Example 21 and 0.9 g (5.6 mmol) of 2,5-dimethoxytetrahydrofuran-3-carbaldehyde were reacted as in Example 17. Yield: 1.5 g (61%), melting point 212°–214° C.

¹H-NMR (D₆-DMSO): δ=3.7 (2H); 6.6 (1H); 7.0 (1H); 7.1–7.4 (6H); 7.6 (1H); 7.7 (1H); 9.8 (1H); 11.5 (broad) and 12.5 (broad) ppm

Example 26

7-(3-Formyl-1-pyrrolyl)-1-(2-methylbenzamido)-6-trifluoromethyl quinoxaline-2,3(1H,4H)-dione

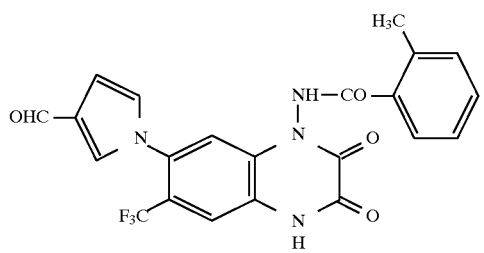

2.7 g (7.1 mmol) of the substance of Example 22 and 1.2 g (7.1 mmol) of 2,5-dimethoxytetrahydrofuran-3-carbaldehyde were reacted as in Example 17. Yield: 2.5 g (77%), melting point 188°–190° C.

¹H-NMR (D₆-DMSO): δ=2.4 (3H); 6.6 (1H); 7.1 (1H); 7.3–7.5 (3H); 7.6 (1H); 7.7 (2H); 7.8 (1H); 9.8 (1H); ca. (11.5 broad) and ca. 12.7 (broad) ppm

Example 27

7-(3-Formyl-1-pyrrolyl)-1-(4-methoxybenzamido)-6-trifluoromethylquinoxaline-2,3(1H,4H)-dione

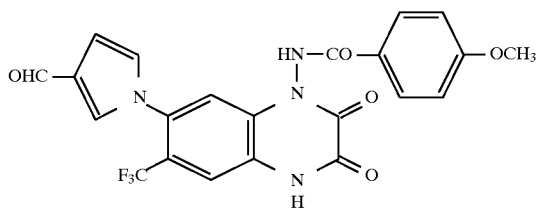

2.1 g (5.3 mmol) of the substance of Example 23 and 0.9 g (5.3 mmol) of 2,5-dimethoxytetrahydrofuran-3-carbaldehyde were reacted as in Example 17. Yield: 2.3 g (92%), melting point >200° C.

¹H-NMR (D₆-DMSO): δ=3.8 (3H); 6.6 (1H); 7.0–7.1 (3H); 7.6 (1H); 7.7 (1H); 7.8 (1H); 8.0 (2H); 9.7 (1H); 11.7 (broad) and 12.7 (broad) ppm

Example 28

7-(3-Formyl-1-pyrrolyl)-6-trifluoromethyl-1-(4-trifluoromethylbenzamido)quinoxaline-2,3(1H,4H)-dione

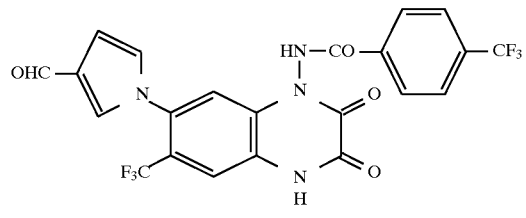

2.5 g (5.8 mmol) of the substance of Example 24 and 0.93 g (5.8 mmol) of 2,5-dimethoxytetrahydrofuran-3-carbaldehyde were reacted as in Example 17. Yield: 2.6 g (89%), melting point >230° C.

¹H-NMR (D₆-DMSO): δ=6.6 (1H); 7.1 (1H); 7.6–7.9 (3H); 8.0 (2H); 8.3 (2H); 9.7 (1H) and ca. 12 (broad) and ca. 12.8 (broad) ppm

Example 29

1-Benzamido-7-(1-pyrrolyl)-6-trifluoromethylquinoxaline-2,3-(1H,4H)-dione

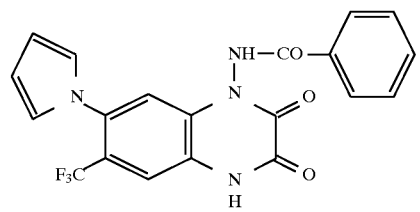

1.4 g (3.8 mmol) of the substance of Example 11 and 0.51 g (38.4 mmol) of 2,5-dimethoxytetrahydrofuran were reacted as in Example 17. Yield: 1.1 g (70%), melting point >250° C.

¹H-NMR (D₆-DMSO): δ=6.2 (2H); 6.9 (2H); 7.3 (1H); 7.5–7.8 (4H); 8.0 (2H) and ca. 12 (broad) ppm

Example 30

1-Benzamido-7-(3-benzamidomethyl-1-pyrrolyl)-6-trifluoromethylquinoxaline-2,3(1H,4H)-dione

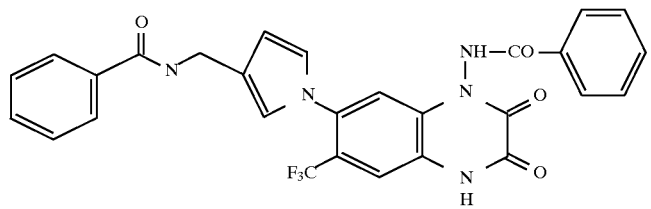

a) N-(2,5-Dimethoxytetrahydrofuran-3-ylmethyl)benzamide 10 g (62 mmol) of 3-aminomethyl-2,5-dimethoxytetrahydrofuran and 17 ml (123 mmol) of triethylamine were dissolved in 100 ml of anhydrous tetrahydrofuran. At 0° C., 7.2 ml (62 mmol) of benzoyl chloride were added dropwise and the mixture was stirred at 0° C. for 1 h. The mixture was filtered and the filtrate was concentrated under reduced pressure. 17 g of crude product were obtained and were immediately reacted further.

b) 1-Benzamido-7-(3-benzamidomethyl-1-pyrrolyl)-6-trifluoromethylquinoxaline-2,3(1H,4H)-dione 1.5 g (4.1 mmol) of the product 11 and 1.2 g (4.5 mmol) of the product obtained in a) were refluxed in 70 ml of acetic acid for 5 min. The mixture was then concentrated under reduced pressure and the resulting oil was crystallized from tetrahydrofuran/ether. Yield: 1.2 g (54%), melting point >190° C. (decomposition).

$^1$H-NMR (D$_6$-DMSO): δ=4.4 (2H); 6.2 (1H); 6.8 (2H); 7.3 (1H); 7.4–8.0 (11H); 8.8 (1H) and ca. 12 (broad) ppm

Example 31

1-Benzamido-7-(3-trifluoroacetamidomethyl-1-pyrrolyl)-6-trifluoromethylquinoxaline-2,3(1H,4H)-dione

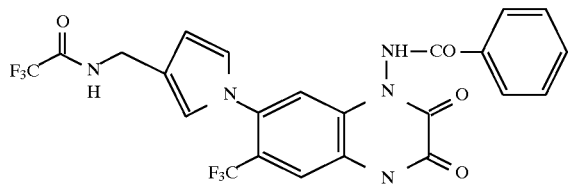

a) Preparation of N-((2,5-dimethoxytetrahydrofuran-3-yl)methyl)trifluoroacetamide 50 g (0.31 mol) of 3-aminomethyl-2,5-dimethoxytetrahydrofuran, 31.7 g (0.31 mol) of triethylamine and a little 4-(N,N-dimethylamino)pyridine were dissolved in 300 ml of anhydrous ether and, at 0° to 5° C., 65.1 g (0.31 mol) of trifluoroacetic anhydride dissolved in 100 ml of anhydrous ether were added dropwise. The mixture was then stirred for 1 h and subsequently washed with water, dried and concentrated under reduced pressure. 70.5 g of impure product were obtained and were reacted further without further purification.

b) 1-Benzamido-7-(3-trifluoroacetamidomethyl-1-pyrrolyl)-6-trifluoromethylquinoxaline-2,3(1H,4H)-dione 3.0 g (8.2 mmol) of the substance of Example 11 and 2.1 g (8.2 mmol) of the product obtained in a) were refluxed in 100 ml of glacial acetic acid for 10 min. The mixture was then concentrated under reduced pressure and the residue was crystallized from ether/petroleum ether. Yield: 4.0 g (91%), melting point 146°–149° C.

$^1$H-NMR (D$_6$-DMSO): δ=4.25 (2H); 6.2 (1H); 6.8 (2H); 7.3 (1H); 7.5–7.8 (4H); 8.0 (2H); 9.75 (1H); 11.8 (1H) and 12.7 (broad) ppm

Example 32

7-(3-Aminomethyl-1-pyrrolyl)-1-benzamido-6-trifluoromethylquinoxaline-2,3(1H,4H)-dione

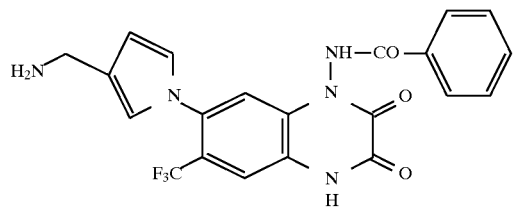

3.5 g (6.5 mmol) of the substance of Example 31 were dissolved in 35 ml of tetrahydrofuran, and 0.47 g (19.5 mmol) of lithium hydroxide dissolved in 50 ml of water were added, and the mixture was stirred at room temperature for 1 h. The tetrahydrofuran was then removed under reduced pressure and the resulting aqueous phase was neutralized with 1M hydrochloric acid. The precipitate was filtered off with suction. Yield: 2.4 g (84%), melting point >250° C.

$^1$H-NMR (D$_6$-DMSO): δ=4.25 (2H); 6.2 (1H); 6.8 (2H); 7.3 (1H); 7.5–7.8 (4H); 8.0 (2H); 9.8 (1H); 11.8 (1H) and 12.8 (broad) ppm

Example 33

N-(1-(1-Benzamido-6-trifluoromethylquinoxaline-2,3(1H,4H)-dion-7-yl)-3-pyrrolyl)methyl-N'-phenylurea

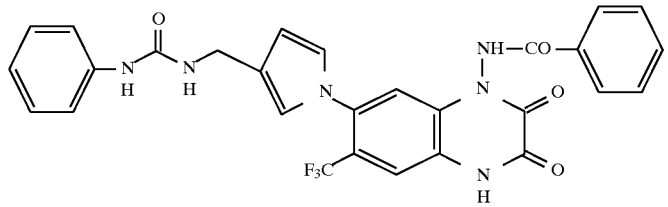

1.1 g (2.5 mmol) of the substance of Example 32, 0.33 g (2.7 mmol) of phenyl isocyanate and a spatula tip of 4-(N,N-dimethylamino)pyridine were heated in 25 ml of dimethylformamide at 120° C. for 15 min. The mixture was then concentrated under reduced pressure and the residue was crystallized from methylene chloride/ether. Yield: 1.1 g (79%), melting point >190° C. (decomposition).

$^1$H-NMR (D$_6$-DMSO): δ=4.1 (2H); 6.2 (1H); 6.25 (1H); 6.7–6.9 (3H); 7.1–7.8 (9H); 8.0 (2H); 8.4 (1H) and ca. 12.2 (broad) ppm

Example 34

1-(2-Methylbenzamido)-7-(3-trifluoroacetamidomethyl-1-pyrrolyl)-6-trifluoromethylquinoxaline-2,3(1H,4H)-dione

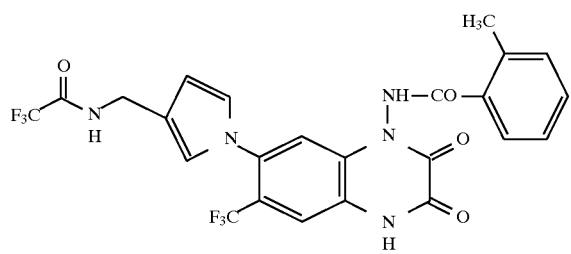

8 g (21.1 mmol) of the substance of Example 22 and 6.5 g (25.3 mmol) of the substance of Example 31a were heated in 200 ml of glacial acetic acid at 110° C. After 30 min, a further 3.3 g (12.6 mmol) of the substance of Example 31a were added, and heating was continued for 15 min. The mixture was then poured into ice-water, and the precipitate was dissolved in ethyl acetate, dried and concentrated under reduced pressure. The residue was treated with ether and filtered off with suction. Yield: 10.1 g (87%), melting point 240°–243° C. (decomposition).

$^1$H-NMR (D$_6$-DMSO): δ=2.4 (3H); 4.25 (2H); 6.1 (1H); 6.8 (2H); 7.2–7.7 (6H); 9.8 (1H) and ca. 11.6 (broad) ppm

Example 35

7-(3-Aminomethyl-1-pyrrolyl)-1-(2-methylbenzamido)-6-trifluoromethylquinoxaline-2,3(1H,4H)-dione

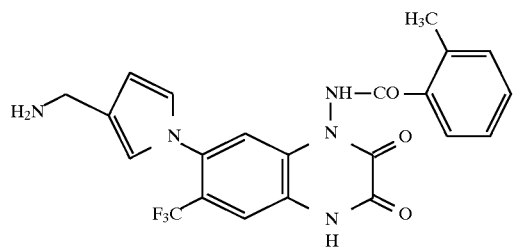

9.5 g (17.1 mmol) of the substance of Example 34 were hydrolyzed with 1.2 g (50.1 mmol) of lithium hydroxide as in Example 32. Yield: 7.0 g (89%), melting point >300° C.

$^1$H-NMR (D$_6$-DMSO): δ=2.3 (3H); 3.9 (2H); ca. 5.5 (2H); 6.3 (1H); 6.8 (1H); 7.0 (1H) and 7.1–7.5 (6H) ppm

Example 36

N-(1-(1-(2-Methylbenzamido)-6-trifluoromethylquinoxaline-2,3(1H,4H)-dion-7-yl)-3-pyrrolyl)methyl-N'-phenylurea

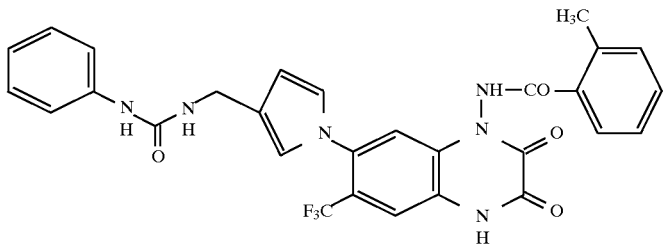

1.5 g (3.3 mmol) of the substance of Example 22 and 0.5 g (4.2 mmol) of phenyl isocyanate were reacted as in Example 33. Yield: 1.1 g (58%), melting point 250°–252° C. (decomposition)

$^1$H-NMR (D$_6$-DMSO): δ=2.3 (3H); 4.2 (2H); 6.2 (1H); 6.3 (1H); 6.8 (2H); 7.1–7.5 (9H); 7.6 (2H); 8.4 (1H) and ca. 12 (broad) ppm

Example 37

N-(1-(1-(2-Methylbenzamido)-6-trifluoromethylquinoxaline-2,3(1H,4H)-dion-7-yl)-3-pyrrolyl)methyl-N'-(4-pyridyl)urea acetate

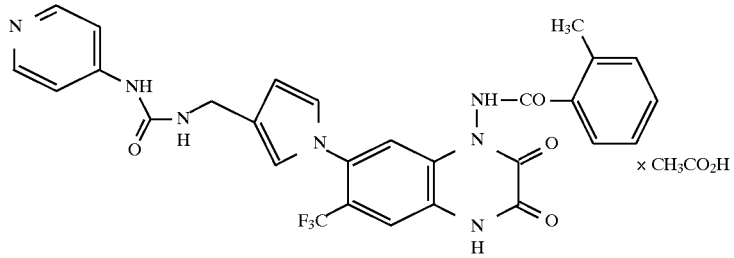

0.45 g (4.8 mmol) of 4-aminopyridine and a spatula tip of 4-(N,N-dimethylamino)pyridine were dissolved in 100 ml of anhydrous dimethylformamide, 0.85 g (5.2 mmol) of 1,1'-carbonyldiimidazole was added, and the mixture was stirred at room temperature for 30 min and then at 50° C. for a further 30 min. 1.5 g (3.3 mmol) of the substance of Example 22 were then added, and the mixture was heated at 90° C. for 1.5 h. After cooling, the dimethylformamide was removed under reduced pressure and the residue was treated with water. The precipitate was filtered off and purified by chromatography (eluent: toluene/acetone/methanol/dimethylformamide/glacial acetic acid=10/7/3/1/1). Yield: 0.56 g (30%), melting point 252°–253° C. (decomposition).

$^1$H-NMR (D$_6$-DMSO): δ=1.9 (3H, acetate); 2.4 (3H); 4.2 (2H); 6.2 (1H); 6.65 (1H); 6.85 (1H); 7.2 (1H); 7.3 (2H); 7.3–7.5 (3H); 7.6 (2H); 8.3 (2H); 9.0 (1H); and 12.0 (broad) ppm

Example 38

7-(3-(4-Benzyl-1-piperazinylmethyl)-1-pyrrolyl)-1-(2-methylbenzamido)-6-trifluoromethylquinoxaline-2,3(1H,4H)-dione

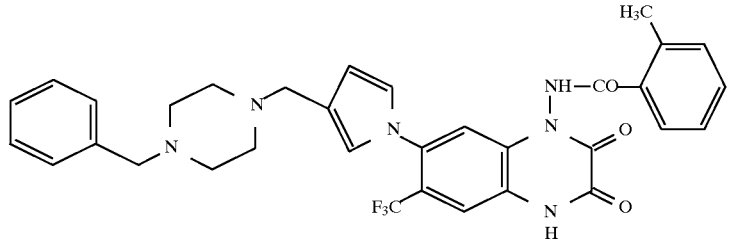

2 g (4.4 mmol) of the substance of Example 26 and 1.6 g (9.1 mmol) of 4-benzylpiperazine were reacted as in Example 19. Yield: 1.7 g (63%), melting point 280°–282° C.

$^1$H-NMR (D$_6$-DMSO): δ=2.4 (3H); 3.2–3.8 (10H); 4.2 (2H); 6.5 (1H); 7.0 (1H); 7.2 (1H); 7.25–7.9 (11H); 11.6 (1H); 12 (broad) and 12.8 (1H) ppm

Example 39

7-(3-Carboxy-1-pyrrolyl)-1-(2-methylbenzamido)-6-trifluoromethylquinoxaline-2,3(1H,4H)-dione

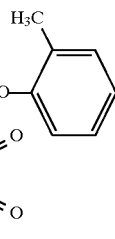

2.0 g (4.4 mmol) of the substance of Example 26 and 0.7 g (2.6 mmol) of 18-crown-6 were refluxed in 100 ml of acetone. Then 1.2 g (4.5 mmol) of potassium permanganate were cautiously added in small portions and the mixture was boiled for 30 min. Subsequently 30 ml of water were added and the mixture was again refluxed for 30 min. Cooling was followed by filtration, and the filtrate was concentrated under reduced pressure. The residue was partitioned between ethyl acetate and aqueous sodium bicarbonate solution. The aqueous solution was acidified with hydrochloric acid and the precipitate was filtered off with suction.

Yield: 0.6 g (29%), melting point 305°–306° C. (decomposition).

$^1$H-NMR (D$_6$-DMSO): δ=2.4 (3H); 6.6 (1H); 7.0 (1H); 7.3 (2H); 7.5 (3H); 7.7 (2H); 11.6 (1H); 12.0 (broad) and 12.7 (broad) ppm

Example 40

N-(1-1-(2-methylbenzamido)-6-trifluoromethylquinoxaline-2,3(1H,4H)-dion-7-yl)-3-pyrrolyl)methyl-N'-(4-nitrophenyl)urea

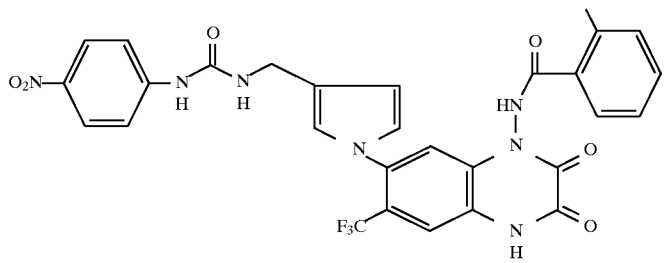

1.5 g (3.3 mmol) of the product from Example 35 and 0.53 g (3.3 mmol) of 4-nitrophenyl isocyanate in 50 ml of anhydrous dimethylformamide were heated at 120° C. for 10 min. The mixture was then concentrated under reduced pressure and the residue was purified by chromatography on silica gel (eluent: toluene/acetone/glacial acetic acid=10/10/0.1). 1.5 g (72%) of the product were obtained.

¹H-NMR (D₆-DMSO): δ=2,4 (3H), 4.2 (2H), 6.2 (1H), 6.7 (1H, NH), 6.8 (2H), 7.2–7.5 (4H), 7.5–7.7 (4H), 8.1 (2H), 9.3 (1H), and ca. 12 (broad) ppm.

Example 41

N'-(4-Ethoxycarbonylphenyl)-N-(1-(1-(2-methylbenzamido)-6-trifluoromethylquinoxaline-2,3(1H,4H)-dion-7-yl)-3-pyrrolyl)methylurea

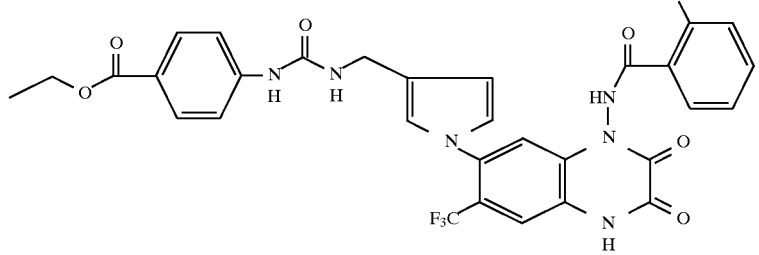

3.5 g (7.7 mmol) of the product from Example 35 and 1.5 g (7.7 mmol) of 4-ethoxycarbonylphenyl isocyanate were reacted as in Example 40. 3.3 g (67%) of the product were obtained, melting point >250° C.

¹H-NMR (D₆-DMSO): δ=1.3 (3H), 2.4 (3H), 4.1–4.4 (4H), 6.2 (1H), 6.5 (1H), 6.8 (2H), 7.2–7.9 (1OH), 8.9 (1H), 11.6 (1H) and 12.5 (1H) ppm.

Example 42

N'-(4-Chlorophenyl)-N-(1-(1-(2-methylbenzamido)-6-trifluoromethylquinoxaline-2,3(1H,4H)-dion-7-yl)-3-pyrrolyl)methylurea

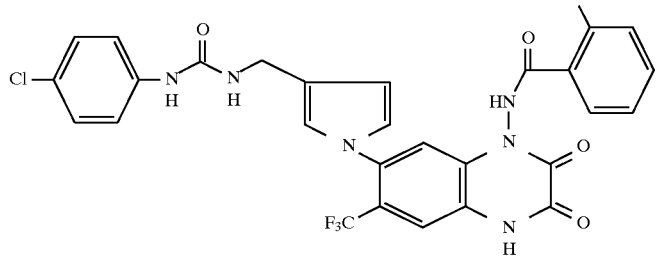

1.6 g (3.5 mmol) of the product from Example 35 and 0.54 g (3.5 mmol) of 4-chlorophenyl isocyanate were reacted as in Example 41. 0.7 g (33%) of the product were obtained, melting point >230° C.

¹H-NMR (D₆-DMSO): δ=2.4 (3H), 4.1 (2H), 6.2 (1H), 6.4 (1H), 6.8 (2H), 7.1–7.7 (11H), 8.7 (1H) and ca. 12 (broad) ppm.

Example 43

N'-(4-Carboxyphenyl)-N-(1-(1-(2-methylbenzamido)-6-trifluoromethylquinoxaline-2,3(1H,4H)-dion-7-yl)-3-pyrrolyl)methylurea

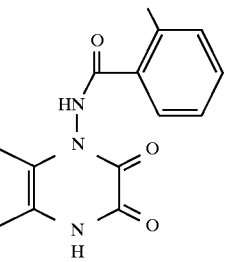

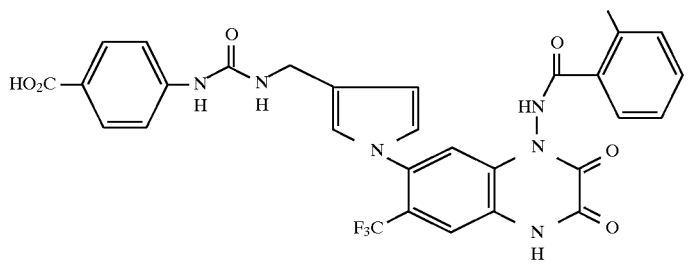

1.5 g (2.3 mmol) of the product from Example 41 were dissolved in 20 ml of tetrahydrofuran, and a solution of 0.17 g (6.5 mmol) of lithium hydroxide in 35 ml of water was added. The mixture was stirred at room temperature for 1 h. The tetrahydrofuran was then removed under reduced pressure, and the resulting aqueous phase was made weakly acidic with 1M hydrochloric acid. The resulting precipitate was filtered off with suction. 1.0 g (70%) of the product was obtained.

$^1$H-NMR (D$_6$-DMSO): δ=2.4 (3H), 4.2 (2H), 6.2 (1H), 6.5 (1H), 6.8 (2H), 7.1–7.9 (11H), 8.9 (1H), 11.6 (1H) and 12.5 (1H) ppm.

Example 44

7-(3-Benzylcarbamoyl-1-pyrrolyl)-1-(2-methylbenzamido)-6-triluoromethylquinoxaline-2,3(1H,4H)-dione

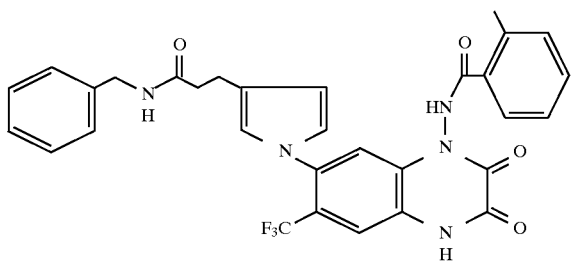

2.0 g (4.2 mmol) of the product from Example 39 were dissolved in 80 ml of anhydrous dimethylformamide, and 0.76 g (4.7 mmol) of carbonyldiimidazole was added. The mixture was stirred at room temperature for 1 h. Then 0.57 g (5.3 mmol) of benzylamine was added. The reaction solution was stirred at room temperature for 16 h and then poured into dilute hydrochloric acid, and the resulting precipitate was filtered off with suction. It was taken up in sodium hydroxide solution and then filtered, and the filtrate was acidified, after which the resulting precipitate was again filtered with suction. 1.6 g (68%) of the product were obtained.

$^1$H-NMR (D$_6$-DMSO): δ=2.4 (3H), 4.4 (2H), 6.7 (1H), 6.9 (1H), 7.1–7.8 (12H), 8.5 (1H), 11.6 (1H) and 12.7 (1H) ppm.

Example 45

1-(2-Methylbenzamido)-7-(3-(4-nitrobenzyl)carbamoyl-1-pyrrolyl)-6-trifluoromethylquinoxaline-2,3(1H,4H)-dione

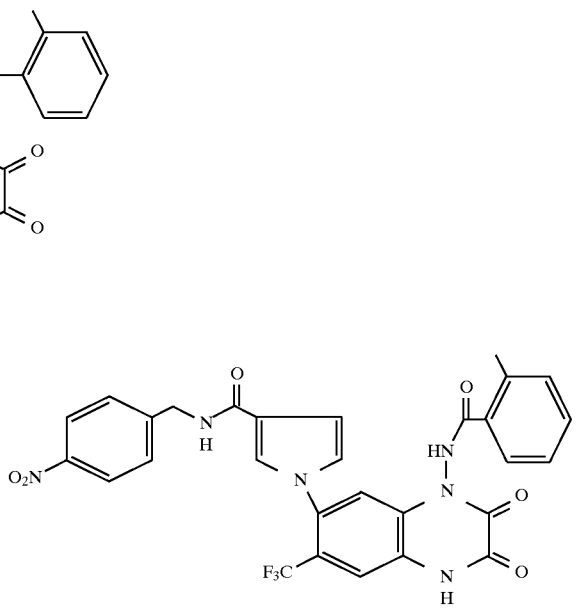

2.0 g (4.2 mmol) of the product from Example 39 and 1.6 g (8.5 mmol) of 4-nitrobenzylamine hydrochloride were reacted as in Example 44. YieldL 1.2 g (47%).

$^1$H-NMR (D$_6$-DMSO): δ=2.4 (3H), 4.5 (2H), 6.7 (1H), 6.9 (1H), 7.2–7.9 (9H), 8.2 (2H), 8.8 (1H), 11.7 (1H) and 12.8 (1H) ppm.

Example 46

7-(3-(4-Chlorobenzyl)carbamoyl-1-pyrrolyl)-1-(2-methylbenzamido)-6-trifluoromethylquinoxaline-2,3(1H,4H)-dione

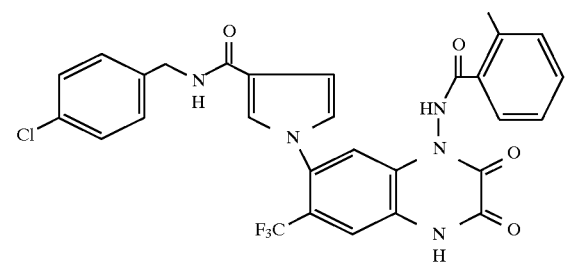

1.0 g (4.2 mmol) of the product from Example 39 and 0.66 g (4.7 mmol) of 4-chlorobenzylamine were reacted as in Example 44. Yield: 1.4 g (56%); melting point >240° C.

$^1$H-NMR (D$_6$-DMSO): δ=2.4 (3H), 4.4 (2H), 6.7 (1H), 6.9 (1H), 7.2–7.5 (9H), 7.7 (2H), 8.5 (1H) and ca. 12 (broad) ppm.

Example 47

O-Benzyl-N-(1-(1-trifluoroacetamido-6-trifluoromethylquinoxaline-2,3(1H,4H)-dion-7-yl)-3-pyrrolyl)methylurethane

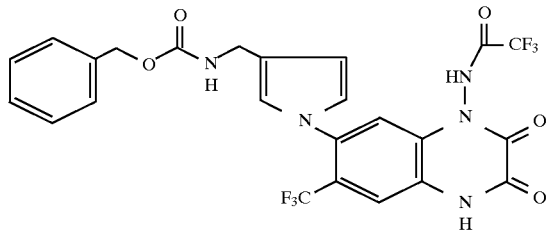 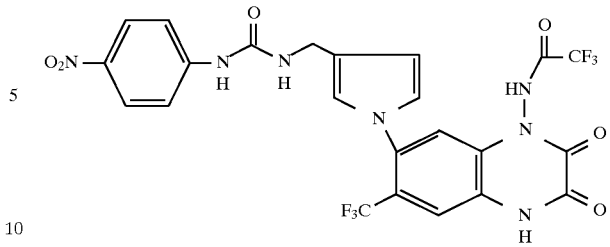

a) O-Benzyl-N-(2,5-dimethoxytetrahydrofuran-3-yl)methylurethane 30 g (0.19 mol) of 3-aminomethyl-2,5-dimethoxytetrahydrofuran (DE 2,645,234) and 51.5 ml (0.37 mol) of triethylamine were dissolved in 250 ml of tetrahydrofuran and, at 0° C., 70 ml (0.21 mol) of 50% strength benzyl chloroformate were added dropwise. The mixture was stirred at 0° C. for 1 h. It was then filtered, and the filtrate was concentrated under reduced pressure. 59 g of the crude product were obtained and were immediately reacted further.

b) O-Benzyl-N-(1-(1-trifluoroacetamido-6-trifluoromethylquinoxaline-2,3(1H,4H)-dion-7-yl)-3-pyrrolyl)methylurethane 63.0 g (0.18 mol) of the product from Example 4 and 52.0 g (0.18 mol) of the product 48a were reacted as in Example 17. 64.8 g (65%) of the product were obtained.

$^1$H-NMR (D$_6$-DMSO): δ=4.1 (2H), 5.0 (2H), 6.6 (1H), 6.8 (2H), 7.0–7.7 (8H) and ca. 12,2 (2H) ppm.

Example 48

7-(3-Aminomethyl-1-pyrrolyl)-1-trifluoroacetamido-6-trifluoromethylquinoxaline-2,3-(1H,4H)-dione

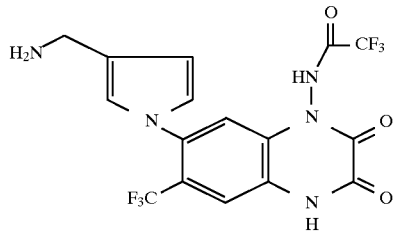

64.0 g (0.11 mol) of the product from Example 47 were dissolved in 500 ml of dimethylformamide and, after addition of 1 g of palladium/carbon (10%), hydrogenated with hydrogen under atmospheric pressure. The mixture was then filtered and the filtrate was concentrated under reduced pressure. 47.3 g (98%) of the product were obtained.

$^1$H-NMR (D$_6$-DMSO): δ=3.9 (2H), 6.3 (1H), 6.9 (1H), 7.0 (1H), 7.2 (1H), 7.2 (1H), 7.6 (1H), 8.0 (3H) and 12.2(1H) ppm.

Example 49

N'-(4-Nitrophenyl)-N-(1-(1-trifluoroacetamido-6-trifluoroethylquinoxaline-2,3(1H,4H)-dion-7-yl)-3-pyrrolyl)-methylurea 15.0 g (34.5 mmol) of the product from Example 48 and 5.7 g (34.5 mmol) of 4-nitrophenyl isocyanate were reacted as in Example 33. 5.3 g (27%) of the product were obtained, melting point >250° C.

$^1$H-NMR (D$_6$-DMSO): δ=4.2 (2H), 6.2 (1H), 6.7 (1H), 6.8 (2H), 7.4 (1H), 7.5 (3H), 8.1 (2H), 9.3 (1H) and 12.5 (1H) ppm.

Example 50

1-Benzamido-9-nitrobenzo[f]quinoxaline-2,3(1H,4H)-dione

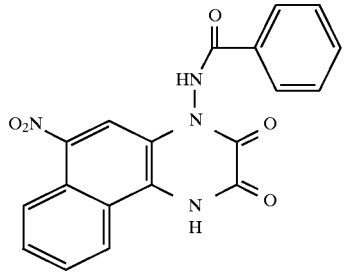

a) N'-(2-Nitro-1-naphthyl)benzhydrazide 0.4 g (2 mmol) of 2-methoxy-1-nitronaphthalene, 0.54 g (4 mmol) of benzhydrazide and 0.54 g (4 mmol) of potassium carbonate in 2 ml of heating fluid (neolab Labothermol®) were heated at 110° C. for 1.5 h. The mixture was then poured into a large amount of water, and the aqueous solution was made weakly acidic with dilute hydrochloric acid and then extracted with ethyl acetate. The organic phase was dried and concentrated under reduced pressure. The residue obtained in this way was purified by chromatography on silica gel (eluent: toluene/acetone=10/1). 0.36 g (60%) of the product were obtained, melting point 183°–184° C. (decomposition).

$^1$H-NMR (D$_6$-DMSO): δ=7.3–8.2 (11H), 9.4(1H) and 20.9 (1H) ppm.

b) Ethyl N-(benzamido)-N-(2-nitro-1-naphthyl)oxamate 0.23 g (1.7 mmol) of ethyl oxalyl chloride was added to 0.5 g (1.6 mmol) of product 50a and 0.17 g (1.7 mmol) of triethylamine in 5 ml of tetrahydrofuran while cooling in ice. After stirring for 2 h, the resulting precipitate was filtered off with suction, and the filtrate was concentrated under reduced pressure. 0.6 g (92%) of the crude product was obtained and was reacted further without purification.

c) 1-Benzamidobenzo[f]quinoxaline-2,3(1H,4H)-dione 0.6 g (1.5 mmol) of product 50b in 20 ml of dimethylformamide was hydrogenated, after the addition of 0.05 g of palladium/carbon (10%), with hydrogen at about 40°–50° C. The mixture was then filtered, and the filtrate was concentrated under reduced pressure. The resulting solid was treated with ethanol and filtered off with suction. 0.45 g (90%) of the product was obtained, melting point >300° C.

$^1$H-NMR (D$_6$-DMSO): δ=7.5–7.7 (6H), 7.8 (1H), 8.0 (1H), 8.1 (2H), 8.7 (1H), 11.8 (broad) and 12.5 (broad) ppm.

d) 22.0 g (66.4 mmol) of the product from Example 50c were dissolved in 30 ml of glacial acetic acid. At 80° C., 35 ml of 65% strength nitric acid were added dropwise. After 5 min, the mixture was cautiously poured into ice-water, and the resulting precipitate was filtered off with suction. 21.3 g (86%) of the product was obtained, melting point >250° C.

$^1$H-NMR (D$_6$-DMSO): δ=7.5–7.9 (5H), 8.1 (2H), 8.4 (2H), 8.8 (1H), 12.0 (1H) and 13 (1H) ppm.

Example 51

1-(2-Methylbenzamido)-9-nitrobenzo[f]quinoxaline-2,3 (1H,4H)-dione

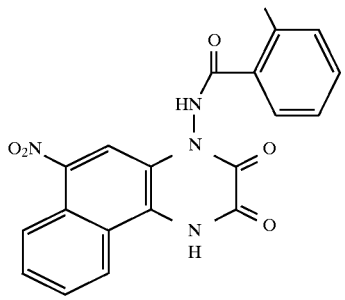

a) 1-Amino-9-nitrobenzo[f]quinoxaline-2,3(1H,4H)-dione 20.0 g (53.2 mmol) of the product from Example 50 were dissolved in 300 ml of concentrated sulfuric acid. Then 50 ml of water were cautiously added dropwise, and the mixture was stirred at 85° C. for 3 h. The reaction mixture was subsequently cautiously poured onto ice, and the resulting precipitate was filtered off with suction. 13.1 g (51%) of the product were obtained, melting point >240° C.

$^1$H-NMR (D$_6$-DMSO): δ=7.75 (2H), 8.5 (1H), 8.8 (2H) and 12.7 (1H) ppm.

b) 1-(2-Methylbenzamido)-9-nitrobenzo[f]quinoxaline-2,3(1H,4H)-dione 5.0 g (18.4 mmol) of the product from Example 51a and 9.3 g (36.7 mmol) of 2-methylbenzoic anhydride in 25 ml of dimethylformamide were heated at 120° C. for 15 min. The mixture was then concentrated under reduced pressure, and the residue was taken up in ethanol and filtered. The filtrate was again concentrated under reduced pressure. 5.3 g (74%) of the product were obtained, melting point >230° C.

$^1$H-NMR (D$_6$-DMSO): δ=2.4 (3H), 7.2–7.9 (7H), 8.4 (1H), 8.6 (1H), 8.9 (1H) and ca. 12 (broad) ppm.

Example 52

9-Amino-1-(2-methylbenzamido)benzo[f]quinoxaline-2,3(1H,4H)-dione

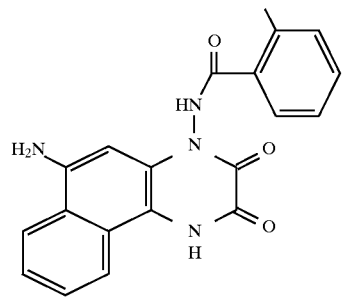

5.0 g (12.8 mmol) of the product from Example 51 in 100 ml of dimethylformamide were hydrogenated, after addition of 0.5 g of palladium/carbon (10%), with hydrogen. The mixture was then filtered, and the filtrate was concentrated under reduced pressure. 4.2 g (92%) of the product were obtained, melting point >240° C.

$^1$H-NMR (D$_6$-DMSO): δ=2.5 (3H), 6.0 (2H, NH$_2$), 6.9 (1H), 7.4–7.7 (5H), 7.8 (1H), 8.1 (1H), 8.5 (1H), 11.5 (1H) and ca. 12.2 (broad) ppm.

Example 53

N'-(4-Ethoxycarbonylphenyl)-N-(1-(1-(2-methylbenzamido) benzo[f]quinoxaline-2,3(1H,4H)-dion-9-yl)-3-pyrrolyl)methylurea

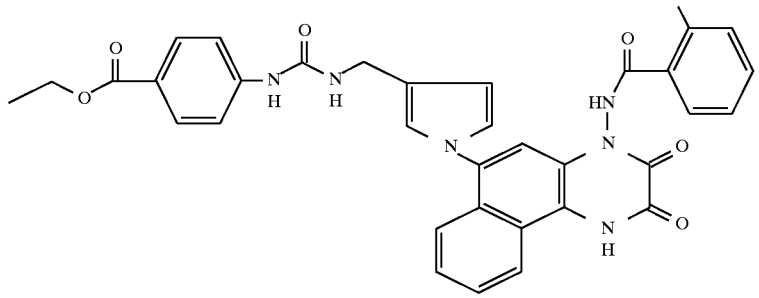

a) N-(2,5-Dimethoxytetrahydrofuran-3-yl)methyl-N'-(4-ethoxycarbonylphenyl)urea 25.0 g (0.15 Mol) of 3-aminomethyl-2,5-dimethoxytetrahydrofuran and 30 g (0.15 mol) of 4-ethoxycarbonylphenyl isocyanate were reacted by method 48a. 57 g of the crude product were obtained and were reacted without purification.

b) N'-(4-Ethoxycarbonylphenyl)-N-(1-(1-(2-methylbenzamido)benzo[f]quinoxaline-2,3(1H,4H)-dion-9-yl)-3-pyrrolyl)methylurea 1.2 g (3.3 mmol) of the product from Example 52 and 1.35 g (3.8 mmol) of product 53a were reacted as in Example 17. 1.3 g (62%) of the product were obtained..

$^1$H-NMR (D$_6$-DMSO): δ=1.3 (3H), 2.45 (3H), 4.3 (4H), 6.3 (1H), 6.6 (1H), 7.0 (2H), 7.3–7.9 (12H), 8.8 (1H), 8.9 (1H), 11.6 (broad) and 12.7 (broad) ppm.

Beispiel 54

N-(1-(1-(2-Methylbenzamido)benzo[f]quinoxaline-2,3(1H,4H)-dion-9-yl)-3-pyrrolyl)methyl-N'-(4-nitrophenyl)urea

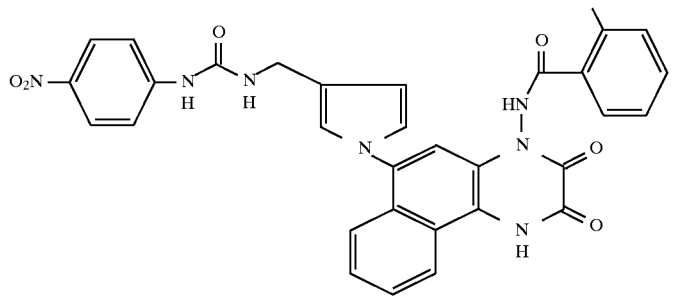

a) N-(2,5-Dimethoxytetrahydrofuran-3-yl)methyl-N'-(4-nitrophenyl)urea 25.1 g (0.15 mol) of 4-nitrophenylurea were dissolved in 150 ml of methylene chloride. The solution was filtered and then 27.0 g (0.17 mol) of 3-aminomethyl-2,5-dimethoxytetrahydrofuran dissolved in 150 ml of methylene chloride were added dropwise at 0° C. The mixture was stirred at room temperature for 1 h and the resulting precipitate was filtered off with suction. 45 g (91%) of the product were obtained. Melting point 172°–174° C.

b) N-(1-(1-(2-Methylbenzamido)benzo[f]quinoxaline-2,3(1H,4H)-dion-9-yl)-3-pyrrolyl)methyl-N'-(4-nitrophenyl)urea 1.2 g (3.3 mmol) of the product from Example 52 and 1.2 g (3.7 mmol) of product 54a were reacted as in Example 17. 0.7 g (35%) of the product was obtained, melting point >230° C.

$^1$H-NMR (D$_6$-DMSO): δ=2.4 (3H), 4.3 (2H), 6.4 (1H), 6.7 (1H), 7.1 (2H), 7.3–7.8 (10H), 8.2 (2H), 8.8 (1H), 9.8 (1H), 11.7 (1H) and 12.7 (1H) ppm.

Example 55

N'-(4-Carboxyphenyl)-N-(1-(1-(2-methylbenzamido)benzo[f]-quinoxaline-2,3(1H,4H)-dion-9-yl)-3-pyrrolyl)methylurea

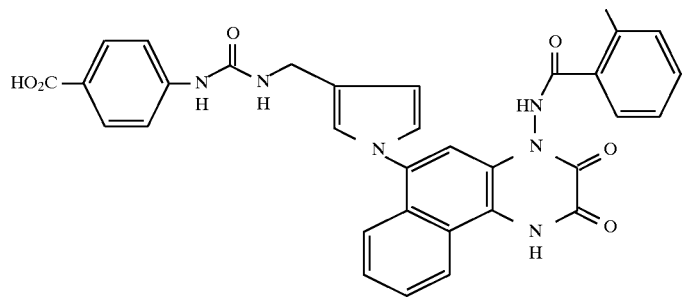

1.1 g (1.7 mmol) of the product from Example 53 were suspended in a solution of 0.13 g (5.2 mmol) of lithium hydroxide in 30 ml of water. The mixture was stirred for 1 h. The clear solution was then made weakly acidic with 1M hydrochloric acid, and the resulting precipitate was filtered off with suction. 0.9 g (82%) of the product was obtained, melting point 225° C. (decomposition).

$^1$H-NMR (D$_6$-DMSO): δ=2.45 (3H), 4.25 (2H), 6.3 (1H), 6.75 (1H), 7.0 (2H), 7.3–8.0 (12H), 8.8 (1H), 9.2 (1H), 11.7 (1H), 12.5 (1H) and 12.7 (1H) ppm.

Example 56

1-Acetamido-7-nitro-6-trifluoromethylquinoxaline-2,3(1H,4H)-dione

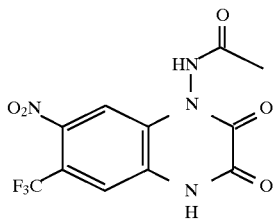

6.5 g (22.4 mmol) of product 3a were refluxed in 60 ml of acetic anhydride for 90 min. The mixture was then concentrated under reduced pressure, and the residue was purified by chromatography on silica gel (eluent: toluene/acetone/acetic acid=10/10/0.1). 4.6 g (62%) of the product were obtained, melting point >250° C.

$^1$H-NMR (D$_6$-DMSO): δ=2.1 (3H), 7.7 (1H), 8.0 (1H), 11.2 (1H) and 12.8 (broad) ppm.

Example 57

1-(3-Methoxycarbonylbenzamido)-7-nitro-6-trifluoromethylquinoxaline-2,3(1H,4H)-dione

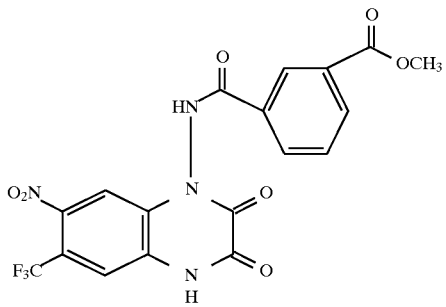

2.5 g (13.9 mmol) of 3-methoxycarbonylbenzoic anhydride and 2.8 g (13.9 mmol) of product 3a were reacted as in method 51b. 2.0 g (61%) of the product were obtained.

$^1$H-NMR (D$_6$-DMSO): δ=3.9 (3H), 7.75 (2H), 8.2–8.4 (3H), 8.6 (1H), 12.2 (broad) and 12.8 (broad) ppm.

Example 58

1-Acetamido-7-amino-6-trifluoromethylquinoxaline-2,3(1H,4H)-dione

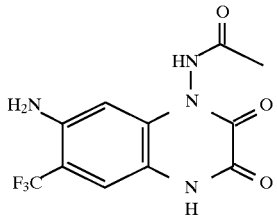

4 g (12.0 mmol) of the product from Example 57 were reacted with 2 g (36.1 mmol) of iron powder as in method 1b. 3.1 g (87%) of the product were obtained, melting point >250° C.

$^1$H-NMR (D$_6$-DMSO): δ=2.1 (3H), 5.6 (2H, NH$_2$), 6.7 (1H), 7.2 (1H), 11.0 (broad) and 12.0 (broad) ppm.

Example 59

1-Acetamido-7-(3-(trifluoroacetamidomethyl)-1-pyrrolyl)-6-trifluoro- methylquinoxaline-2,3(1H,4H)-dione

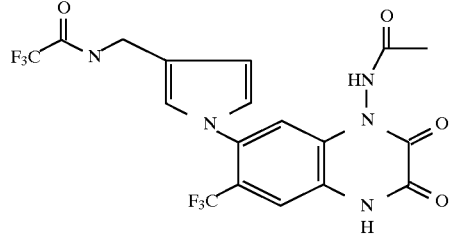

2.45 g (8.1 mmol) of the product from Example 58 and 2.2 g (8.5 mmol) of product 31a were reacted as in method 31b. 3.1 g (87%) of the product were obtained, melting point >242° C.

$^1$H-NMR (D$_6$-DMSO): δ=2.1 (3H), 4.3 (2H), 6.2 (1H), 6.8 (2H), 7.3 (1H), 7.6 (1H), 9.8 (1H), 11.2 (1H) and 12.5 (1H) ppm.

Example 60

1-Acetamido-7-(3-aminomethyl-1-pyrrolyl)-6-trifluoromethylquinoxaline-2,3(1H,4H)-dione

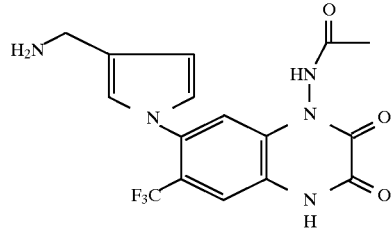

2.5 g (5.2 mmol) of the product from Example 59 were hydrolyzed with lithium hydroxide as in Example 32. 1.7 g (84%) of the product were obtained.

$^1$H-NMR (D$_6$-DMSO): δ=2.1 (3H), 3.8 (2H), 6.5 (1H), 6.9 (1H), 7.05 (1H), 7.1 (1H) and 7.9 (1H) ppm.

Example 61

N-(1-(1-Acetamido-6-trifluoromethylquinoxaline-2,3(1H,4H)-dion-7-yl)-3-pyrrolyl)methyl-N'-(4-ethoxycarbonylphenyl)urea

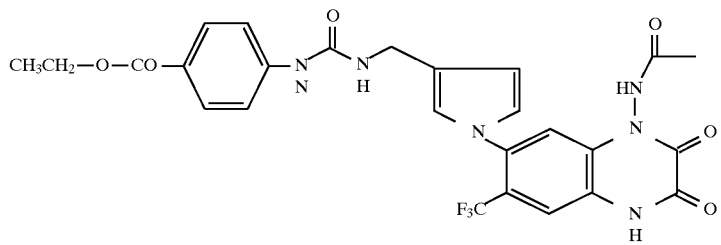

1.7 g (4.5 mmol) of the product from Example 60 and 1.0 g (5.2 mmol) of 4-ethoxycarbonylphenyl isocyanate were reacted as in Example 33. 1.5 g (58%) of the product were obtained, melting point >230° C.

$^1$H-NMR (D$_6$-DMSO): δ=1.3 (3H), 2.1 (3H), 4.2 (2H), 4.25 (2H), 6.2 (1H), 6.5 (1H), 6.8 (1H), 7.2 (1H), 7.5 (2H), 7.6 (1H), 7.8 (2H), 8.9 (1H), 11.1 (broad) and 12.5 (broad) ppm.

Example 62

N-(1-(1-Acetamido-6-trifluoromethylquinoxaline-2,3(1H,4H)-dion-7-yl)-3-pyrrolyl)methyl-N'-(4-carboxyphenyl)urea

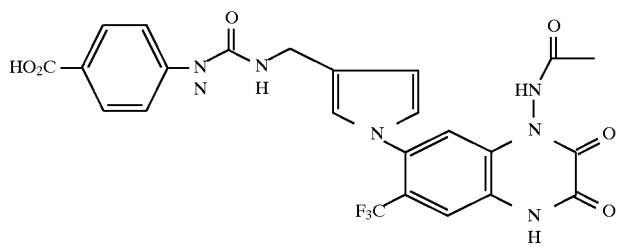

1.0 g (1.8 mmol) of the product from Example 61 was hydrolyzed with lithium hydroxide as in Example 55. 0.7 g (74%) of the product was obtained.

$^1$H-NMR (D$_6$-DMSO): δ=2.1 (3H), 4.2 (2H), 6.2 (1H), 6.5 (1H), 6.8 (2H), 7.2 (1H), 7.5 (2H), 7.7 (1H), 7.8 (2H), 11.1 (1H) and 12.2 (1H) ppm.

We claim:

1. An amido-quinoxalinedione of the formula I

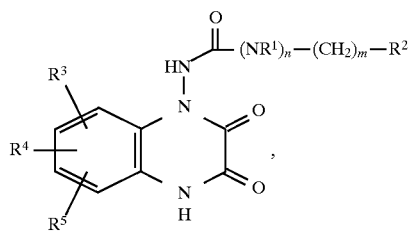

where $R^1$ is hydrogen or $C_1$–$C_4$-alkyl, n is 0 or 1, m is 0, 1, 2, 3 or 4, $R^2$ is methyl or phenyl, which can be substituted by one or two straight-chain $C_1$–$C_4$-alkyl radicals, $R^3$ is

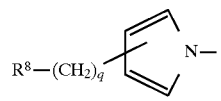

where q is 0 and $R^8$ is H, —COO(CH$_2$)$_r$R$^{10}$, —CONH(CH$_2$)$_r$R$^{10}$, —CH$_2$—NR$^{10}$R$^{11}$, —CH$_2$NH—CY—(CH$_2$)$_r$R$^{11}$, —CH=NOR$^{10}$, —CH$_2$—NH—CY—Z—(CH$_2$)$_r$R$^{11}$, —CH$_2$—NH—Co—CF$_3$, or

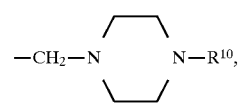

where Y is O

Z is NH and $R^{10}$ is hydrogen, straight-chain or branched $C_1$–$C_4$-alkyl, phenyl, benzyl, pyridyl or benzhydryl, r is 0, 1, 2, 3 or 4 and $R^{11}$ is hydrogen, straight-chain or branched $C_1$–$C_4$-alkyl, phenyl, or

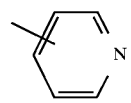

and the benzene rings present in $R^8$, $R^{10}$ and $R^{11}$ can also be substituted by one or two of the following radicals: NH$_2$, OCH$_3$, OCH$_2$CH$_3$, Cl, Br, OCF$_3$, F, CH$_3$, C$_2$H$_5$, NO$_2$, —COOR$^1$ or —CONHR$^1$ and $R^4$ and $R^5$ which can be identical or different, are hydrogen, trifluoromethyl, or a fused-on benzene ring and the tautomeric, isomeric and enatiomeric forms thereof and the physiologically tolerated salts thereof.

2. A method for treating neurodegenerative disorders and neurotoxic disturbances which comprises administering to a host a pharmocologically effective amount of a compound as defined in claim 1.

3. A pharmaceutical composition for oral, parenteral or intraperitoneal use, comprising, besides conventional pharmaceutical ancillary substances, per single dose from 0.1 to 100 mg of at least one amido-quinoxalinedione I as claimed in claim 1 per kg of body weight.

* * * * *